United States Patent [19]

Hirano et al.

[11] Patent Number: 5,350,919
[45] Date of Patent: Sep. 27, 1994

[54] QUANTITATIVE ANALYZING METHOD BY A SECONDARY ION MASS SPECTROMETRIC METHOD AND A SECONDARY ION MASS SPECTROMETER

[75] Inventors: Takashi Hirano; Takeshige Tanigaki; Hideki Kimura, all of Kanagawa, Japan

[73] Assignee: Sony Corporation, Tokyo, Japan

[21] Appl. No.: 84,476

[22] Filed: Jul. 1, 1993

[30] Foreign Application Priority Data

Sep. 17, 1991 [JP] Japan .............................. 3-265172
Jul. 7, 1992 [JP] Japan .............................. 4-202975

[51] Int. Cl.$^5$ .............................................. H01J 49/26
[52] U.S. Cl. ........................................ 250/282; 250/281; 250/252.1
[58] Field of Search ................. 250/281, 282, 252.1 R

[56] References Cited

PUBLICATIONS

Leta et al., *Analytical Chemistry*, vol. 52, No. 3, Mar. 1980, pp. 514–519.
Werner, *Acta Electronica*, 18, 1, 1975, pp. 51–62.

*Primary Examiner*—Jack I. Berman
*Attorney, Agent, or Firm*—Hill, Steadman & Simpson

[57] ABSTRACT

A quantitative analyzing method by a secondary ion mass spectrometric method comprises the steps of: quantitatively analyzing the target element by the secondary ion mass spectrometric method with respect to a plurality of ion-implanted standard samples, while changing an implantation energy; and correcting a secondary ion intensity which is obtained with respect to the target element in the surface layer of the sample to be analyzed by the secondary ion mass spectrometric method on the basis of the results of the quantitative analyses with respect to the plurality of standard samples. A secondary ion mass spectrometer having such a function is also disclosed.

3 Claims, 25 Drawing Sheets

QUANTITATIVE ANALYZING METHOD BY A SECONDARY ION MASS SPECTROMETRIC METHOD AND A SECONDARY ION MASS SPECTROMETER

BACKGROUND OF THE INVENTION

1. Field of the Invention

The invention relates to a quantitative analyzing method by a secondary ion mass spectrometric method and to a secondary ion mass spectrometer. More particularly, the invention is suitable when it is applied to the case of quantitatively analyzing elements of a surface layer of a sample.

2. Description of the Prior Art

A secondary ion mass spectrometric (SIMS) method is an analyzing method having ultrahigh sensitivity characteristics (to ppb level) and high resolution characteristics (to 1 nm) in the depth direction. For example, in the semiconductor field, such an SIMS method is highlighted as an analyzing method which is most useful in case of knowing a concentration distribution of doping impurities in an ultrashallow region due to implantation of ultralow energy ions.

According to the SIMS method, a primary ion beam which has been thinly converged is irradiated onto the surface of a sample to thereby eject out the atoms in the sample, and a part of the ionized particle group, namely, secondary ions are mass analyzed. Generally, as an energy of the primary ions, an energy in a range from a few keV to about 20 keV in which a sputtering yield is high is used. According to the SIMS method, therefore, the analytic region is peeled off one layer by one every time and an ion implantation phenomenon occurs in the depth direction in such a region.

On the other hand, an occurrence probability the secondary ions of a certain special element by the primary ions, namely, a yield of the secondary ions is strongly dominated by a peculiar ionizing potential, a work function of the sample surface, or the like. In other words, the secondary ion yield largely depends on a mother material (matrix) of the sample, coexisting element species, and chemical states of the uppermost surface of a sample, or the like.

In the actual analysis by the SIMS method, molecule-like or atom-like oxygen ions ($^{32}O_2^+$, $^{16}O^-$, etc.) are often used as primary ion species. In this case, however, since the oxygen concentration does not reach an equilibrium state up to a certain depth (critical depth $D_x$) from the uppermost surface of the sample, the secondary ion yield is also changed every time. Such a phenomenon is called a primary ion implantation effect. Or, such a primary ion implantation effect can be also said as a phenomenon such that the primary ions are implanted into the uppermost layer of the sample and the secondary ion yield is changed every time in dependence on the concentration distribution. In any case, due to the primary ion implantation effect, it is difficult to interpret an intensity of the secondary ions which are obtained in the region of a depth $X \leq D_x$ from the uppermost surface of the sample. It is, thus, impossible to quantitatively analyze the elements such as impurities or the like in the surface layer of the sample.

Many methods have been proposed so far to solve the above problem.

The first method is a method whereby the secondary ion intensity of a target element which was actually measured is normalized by using the secondary ion intensity of the matrix which was simultaneously actually measured at each depth position and a concentration is calculated on the basis of the normalized secondary ion intensity.

The second method is a method whereby an arbitrary film (in case of a sample of Si, a polycrystalline Si film or an amorphous Si film) having a thickness of 50 to 100 nm is previously formed on the surface of a sample to be analyzed, a region which is influenced by the primary ion implantation effect is shut into such a film, and the secondary ion yield in the region as a target of the analysis is kept constant.

The third method is a method whereby an oxygen gas is purposely introduced into an analyzing chamber of the SIMS at a pressure of up to $10^{-3}$ Pa and an oxygen atmosphere is formed, thereby indirectly eliminating the formation of the region which is influenced by the primary ion implantation effect, and thereby suppressing a change in secondary ion yield due to a depth position and keeping the secondary ion yield constant.

The above first method is effective only in the case where the changing state of the secondary ion yield due to the depth position is equal without depending on the secondary ion species. However, since such an assumption is not generally satisfied, the first method is nothing but a simple convenient method.

According to the above second method, a film cannot always be formed prior to the SIMS analysis and, further, there is a fear of occurrence of a change in impurity distribution due to contamination or thermal disturbance in association with such a film formation.

The third method is, further, not so preferable because when oxygen is purposely introduced into the analyzing chamber, such an introduction will exert an adverse influence on the subsequent analysis.

OBJECTS AND SUMMARY OF THE INVENTION

It is, therefore, an object of the present invention to provide a quantitative analyzing method by a secondary ion mass spectrometric method in which a target element in the surface layer of a sample can be quantitatively analyzed without executing a pre-treatment of the sample such as a film formation or the like, an improvement of an apparatus, or the like.

Another object of the invention is to provide a secondary ion mass spectrometer which can quantitatively analyze a target element in the surface layer of a sample.

According to an aspect of the invention, there is provided a quantitative analyzing method by a secondary ion mass spectrometric method whereby a target element in a sample to be analyzed is quantitatively analyzed by the secondary ion mass spectrometric method, comprising the steps of:

quantitatively analyzing the target element by the secondary ion mass spectrometric method with respect to a plurality of ion-implanted standard samples, while changing an implantation energy; and correcting a secondary ion intensity which is obtained with respect to the target element in the surface layer of the sample to be analyzed by the secondary ion mass spectrometric method on the basis of the results of the quantitative analyses with respect to the plurality of standard samples.

According to the quantitative analyzing method by a secondary ion mass spectrometric method of the present invention, an influence by the primary ion implantation effect in the surface layer of a sample to be analyzed can be eliminated by the correction based on the result of the quantitative analysis by the secondary ion mass spectrometric method regarding a standard sample, so that a target element in the surface layer of the sample to be analyzed can be quantitatively analyzed. In this case, moreover, there is no need to execute a pretreatment of the sample such as film formation, an improvement of the apparatus, or the like.

According to another aspect of the invention, there is provided a secondary ion mass spectrometer having a function such that a secondary ion intensity which is obtained with respect to a target element in the surface layer of a sample to be analyzed by a secondary ion mass spectrometric method is corrected on the basis of results such that the target element was quantitatively analyzed by the secondary ion mass spectrometric method with respect to a plurality of ion-implanted standard samples, while changing an implantation energy.

According to the secondary ion mass spectrometer of the present invention, a secondary ion intensity distribution which was actually measured with respect to a sample to be analyzed can be corrected on the basis of the result of the quantitative analysis by a secondary ion mass spectrometric method about a standard sample, so that an influence by the primary ion implantation effect in the surface layer of the sample to be analyzed can be eliminated. Thus, a target element in the surface layer of the sample to be analyzed can be quantitatively analyzed.

The above, and other, objects, features and advantage of the present invention will become readily apparent from the following detailed description thereof which is to be read in connection with the accompanying drawings.

DETAILED DESCRIPTION OF THE PREFERRED EMBODIMENTS

An embodiment of the present invention will be described hereinbelow with reference to the drawings.

Prior to explaining the embodiment, the necessity of the quantitative correction of the analysis data by SIMS will be again described and the correlations between the regions which are influenced by the primary ion implantation effect and various amounts will be described.

Generally, in the quantitative analysis by the SIMS method, not only an unknown sample but also a concentration standard sample formed by implanting ions into a matrix of the same quality as that of the unknown sample of the like are prepared and both of them are SIMS analyzed under the same conditions. Now, assuming that an intensity of the secondary ion of a specific mass of an element (j) contained in a certain solid sample is set to $I_j$, it is given by the following equation (1).

$$I_j = \eta \cdot S \cdot Y_j \cdot C_j \cdot I_p \tag{1}$$

where $I_p$ is the primary ion current, $\eta$ is the secondary ion transmission factor, S is the sputtering ratio $Y_j$ is the secondary ion yield of the element (j), and $C_j$ is the concentration (atom concentration) of the element (j).

In this case, it is ordinarily assumed that four factors ($\eta$, S, $Y_j$, $I_p$) of the right side of the equation (1) of the unknown sample are respectively equal to those of the standard sample and they are handled in a lump as a relative sensitivity coefficient K. However, an assumption such that "the secondary ion yield $Y_j$ is constant without depending on the depth position of the sample" is included in the above assumption. As already mentioned above, however, such an assumption is never satisfied in the surface layer which is influenced by the primary ion implantation effect. A necessity of some quantitative correction now occurs.

As mentioned above, both of the sputtering phenomenon and the primary ion implantation effect simultaneously occur under the ordinary SIMS conditions.

Figure 1:
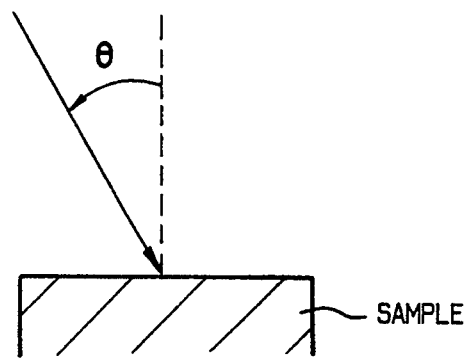
FIG. 1 is a schematic diagram showing an irradiation angle of a primary ion onto the surface of a sample in the SIMS method.

It is now assumed that an attention is paid to the sample surface (this surface is called an effective surface and distance from the initial surface is set to X) which is exposed after the elapse of a time t just after the primary ion beam was irradiated and a concentration of the implanted ions (oxygen ions) at that position is set to $C_s$. The concentration $C_s$ is generally given by the following equation (2).

$$C_S = \frac{J_p \cos\theta}{q \cdot V_s} \left\{ erf\left(\frac{V_s \cdot t - R_P}{2\Delta R_P}\right) + erf\left(\frac{R_F}{2\Delta R_P}\right) \right\} \tag{2}$$

where $J_p$ is the primary ion current density, $V_s$ is the sputtering rate, $R_p$ is the projected range of the primary ion, $\Delta R_p$ is the projected standard deviation of the primary ion, $\theta$ is the irradiation angle of primary ion (incident angle) (refer to FIG. 1), and q is the unit charge.

Although $V_s \propto J_p$ and $X = \int V_s(t)dt$ are generally satisfied, it is assumed that $V_s$ is constant in the following description for simplicity.

Factors in { } in the equation (2) give a distribution shape near the surface until a concentration reaches a saturation concentration $K_0$ ($C_s \to K_0$ for t $\infty$). Factors out of { } give the absolute value.

Figure 2:
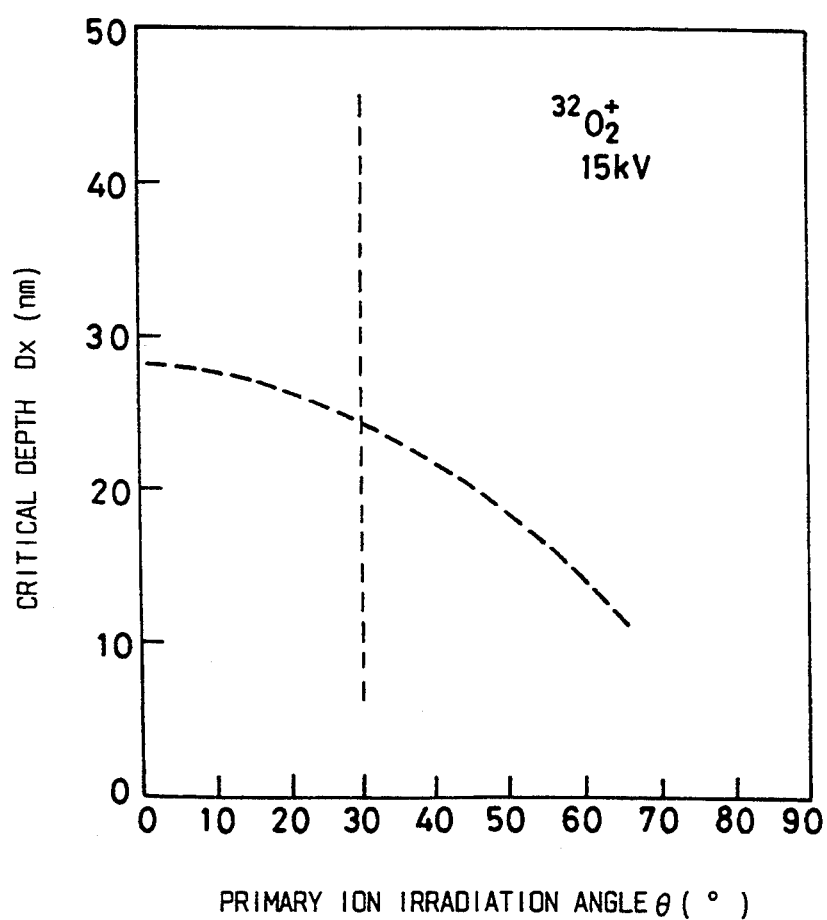
FIG. 2 is a graph showing a dependency of a critical depth on the primary ion irradiation angle.
Figure 3:
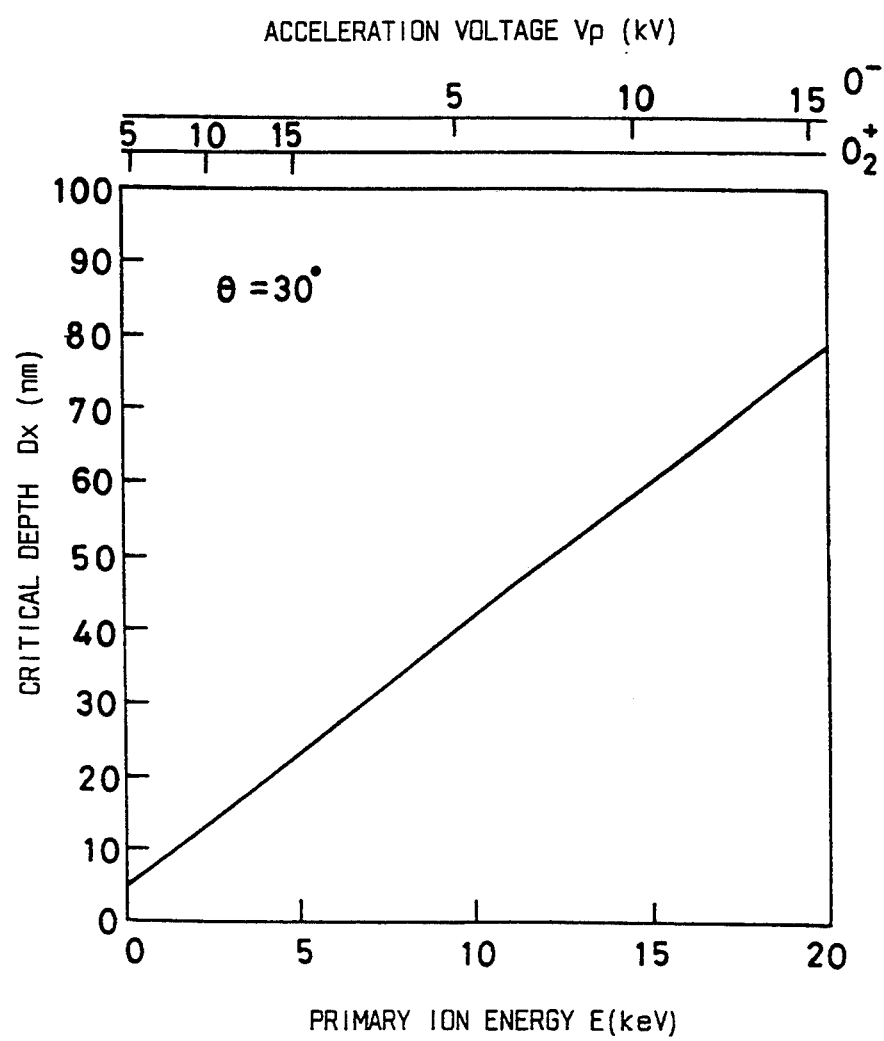
FIG. 3 is a graph showing a dependency of the critical depth on a primary ion energy.
Figure 4:
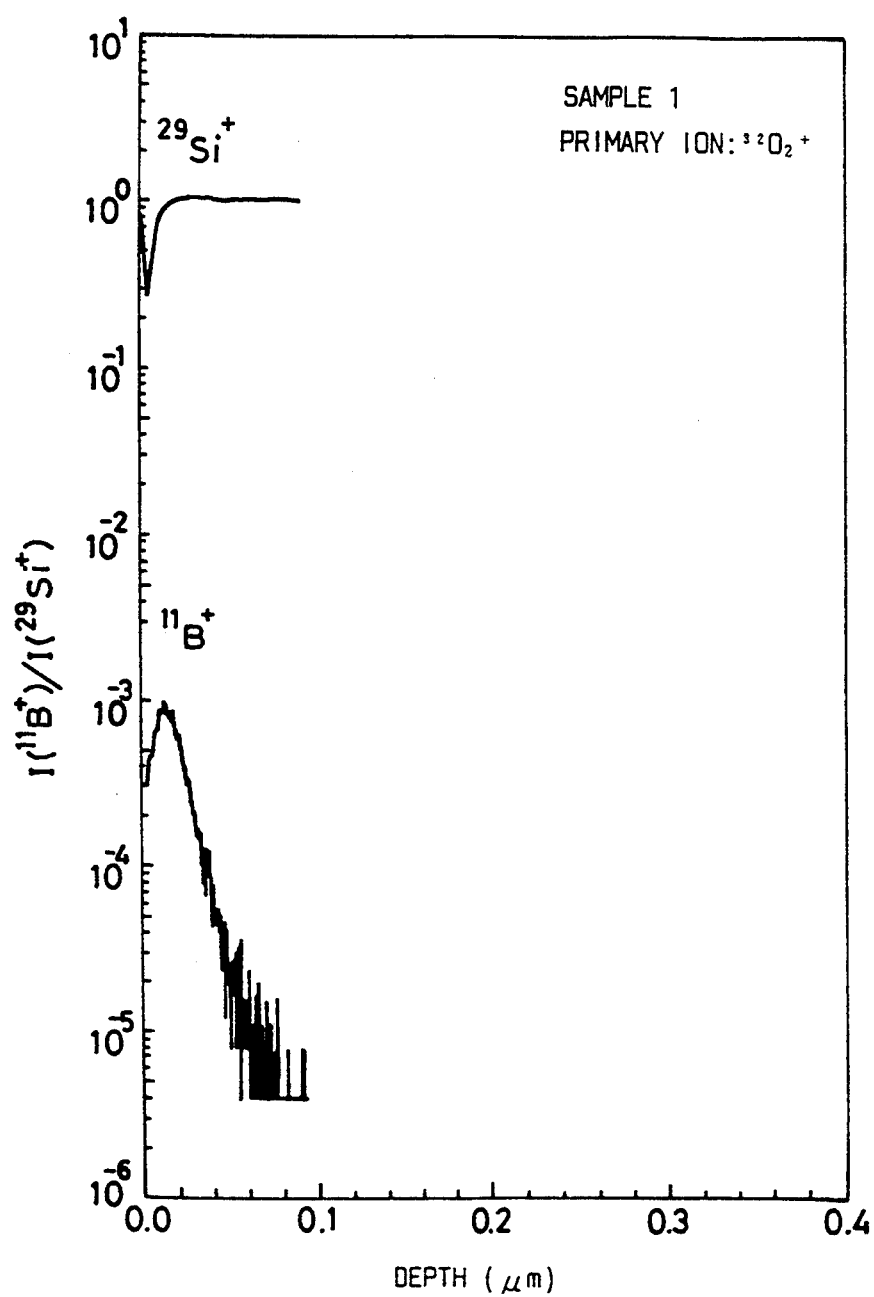
FIG. 4 is a graph showing a $^{11}B+/^{29}Si+$ relative secondary ion intensity distribution obtained by an SIMS analysis regarding a standard sample 1 in an embodiment of the invention.
Figure 5:
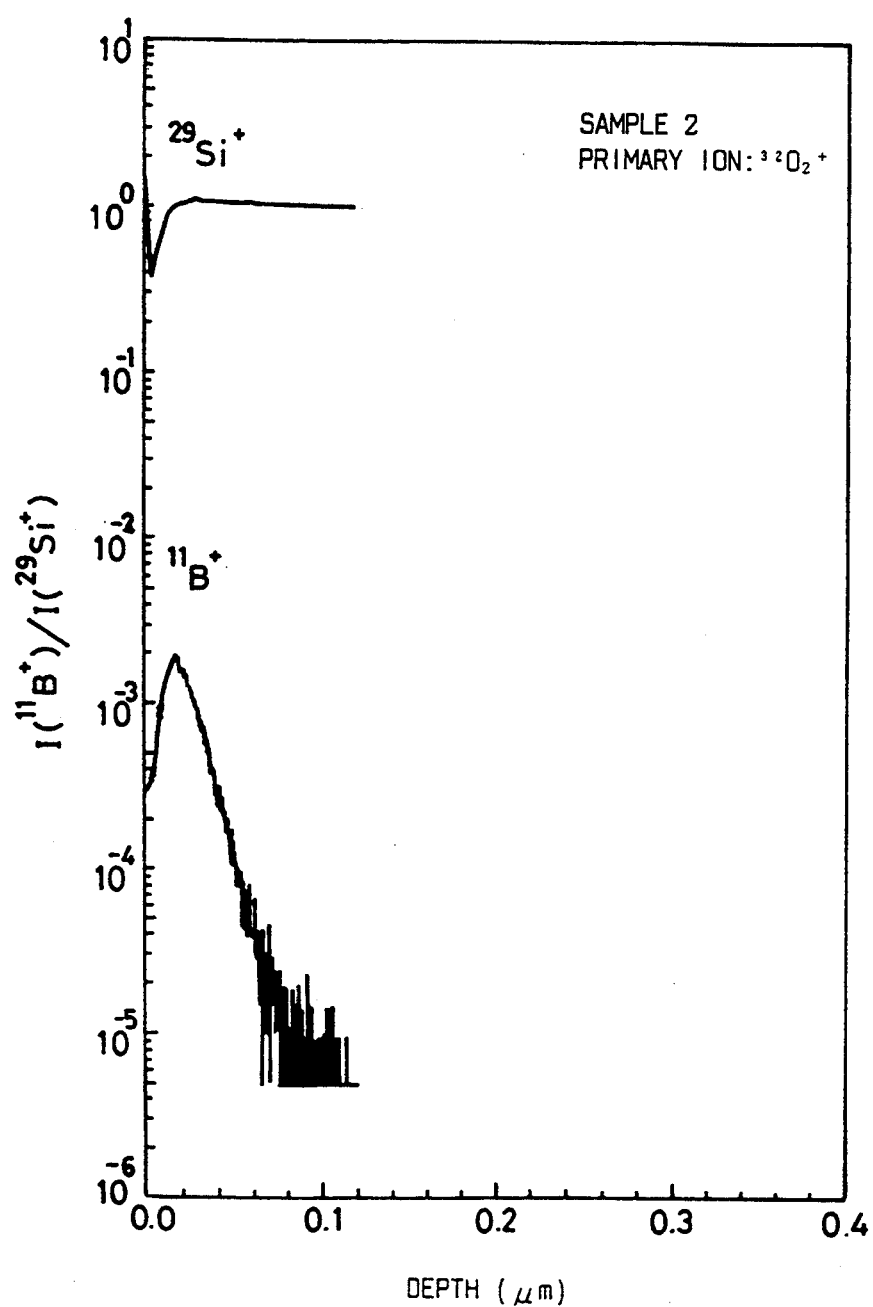
FIG. 5 is a graph showing a $^{11}B+/^{29}Si+$ relative secondary ion intensity distribution obtained by an SIMS analysis regarding a standard sample 2 in an embodiment of the invention.
Figure 6:
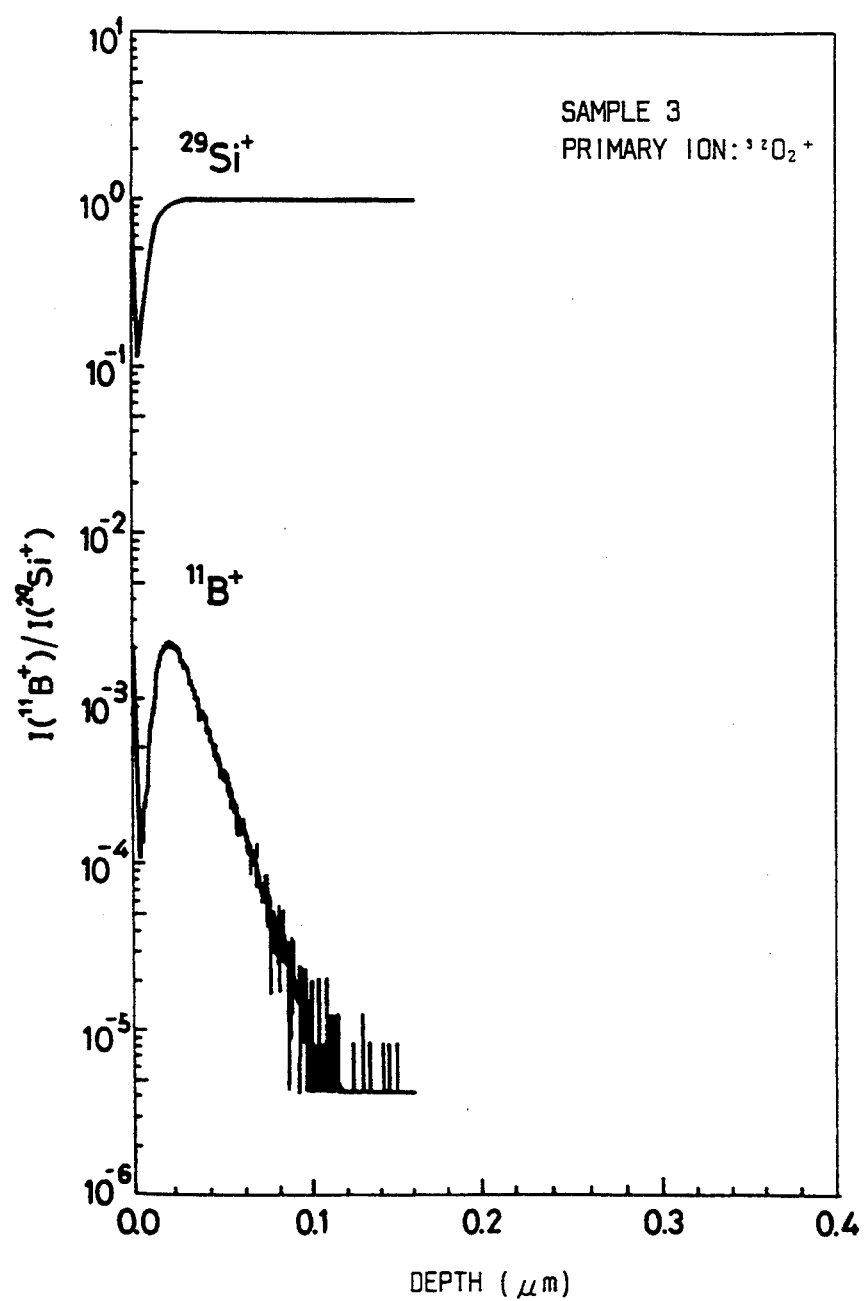
FIG. 6 is a graph showing a $^{11}B+/^{29}Si+$ relative secondary ion intensity distribution obtained by an SIMS analysis regarding a standard sample 3 in an embodiment of the invention.
Figure 7:
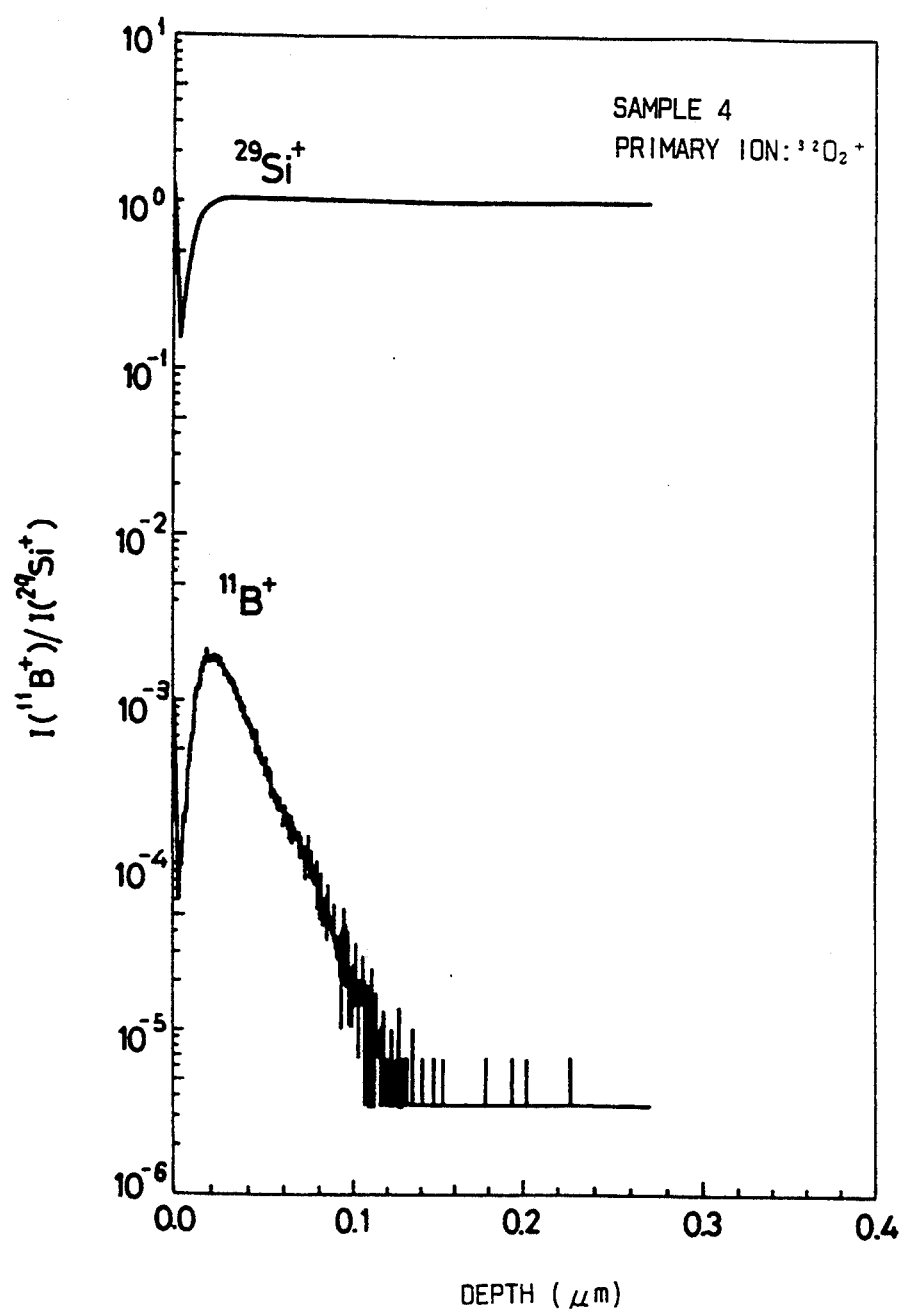
FIG. 7 is a graph showing a $^{11}B+/^{29}Si+$ relative secondary ion intensity distribution obtained by an SIMS analysis regarding a standard sample 4 in an embodiment of the invention.
Figure 8:
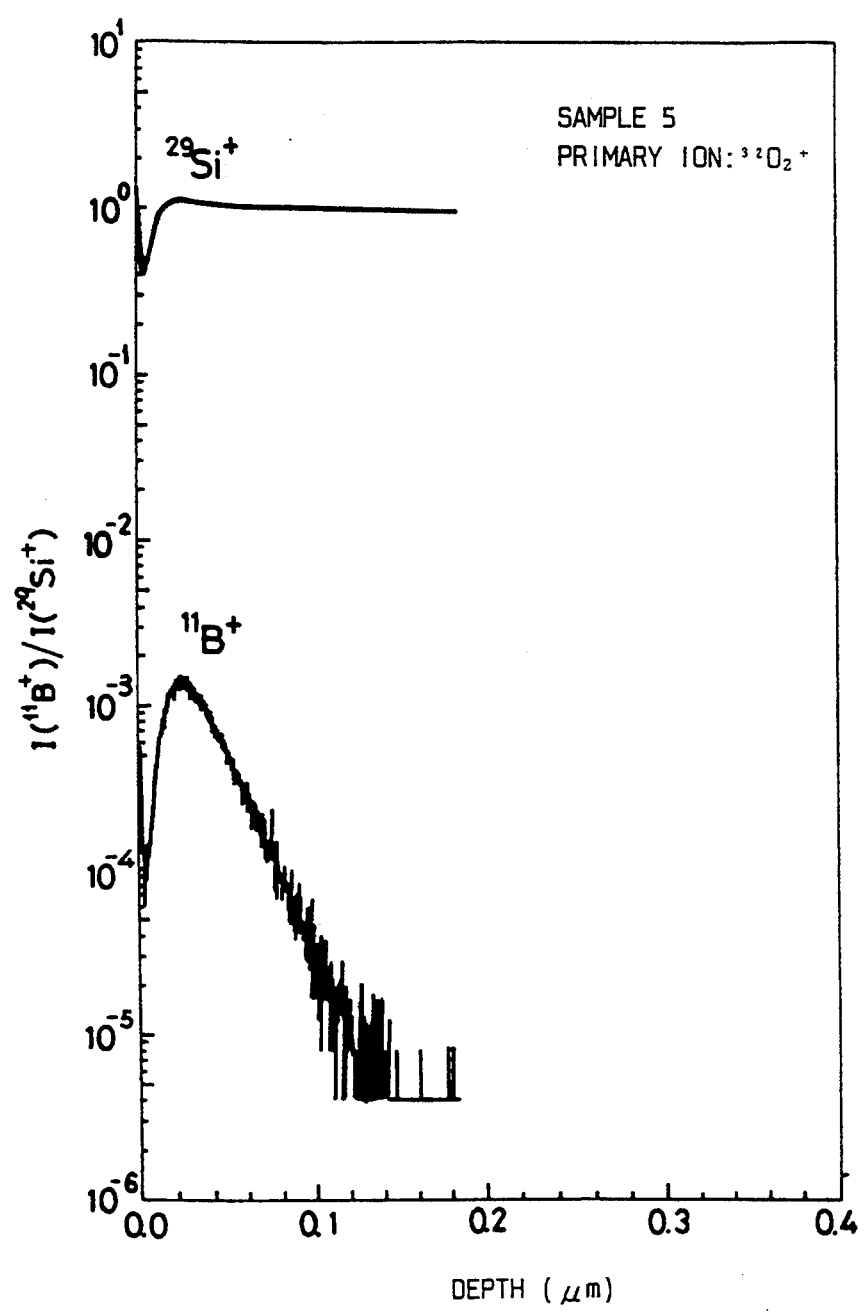
FIG. 8 is a graph showing a $^{11}B+/^{29}Si+$ relative secondary ion intensity distribution obtained by an SIMS analysis regarding a standard sample 5 in an embodiment of the invention.
Figure 9:
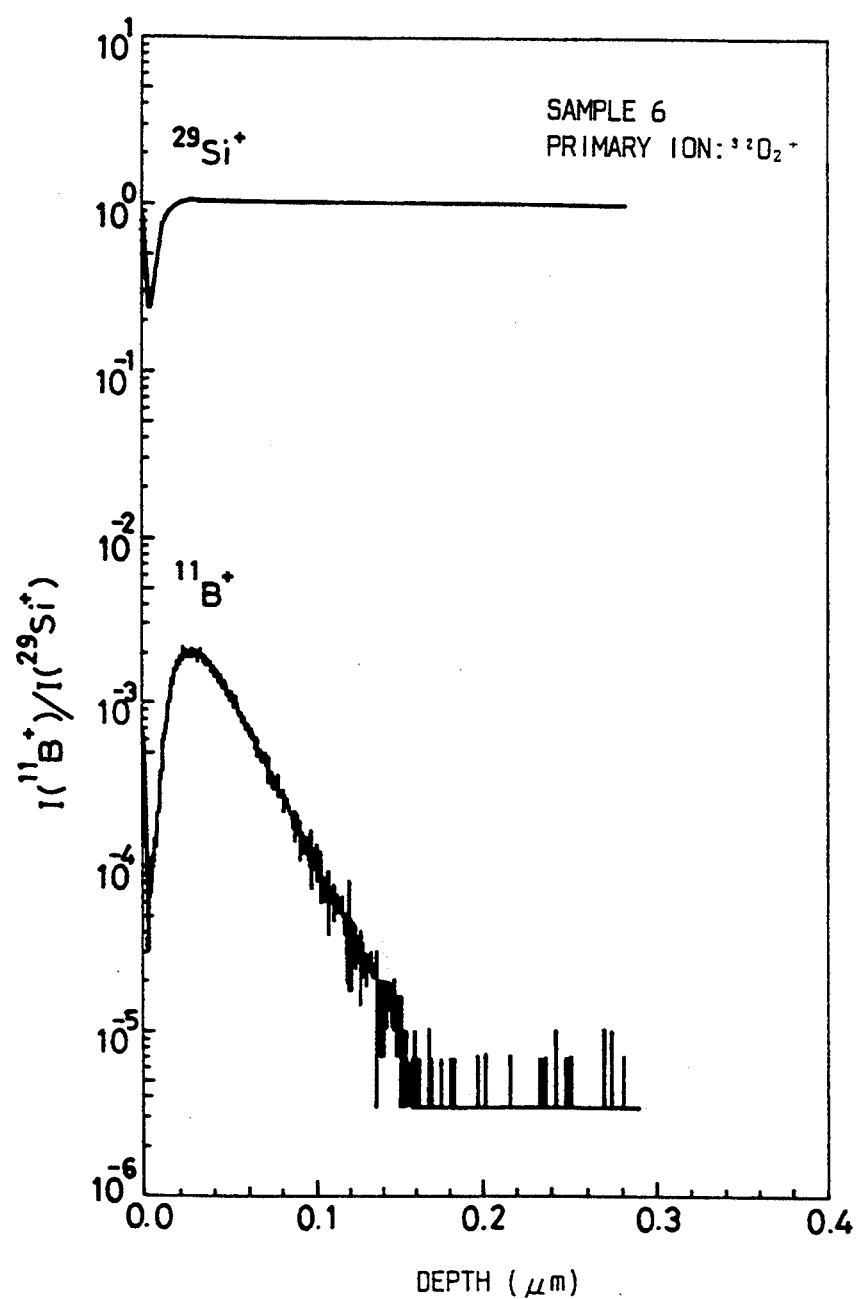
FIG. 9 is a graph showing a $^{11}B+/^{29}Si+$ relative secondary ion intensity distribution obtained by an SIMS analysis regarding a standard sample 6 in an embodiment of the invention.
Figure 10:
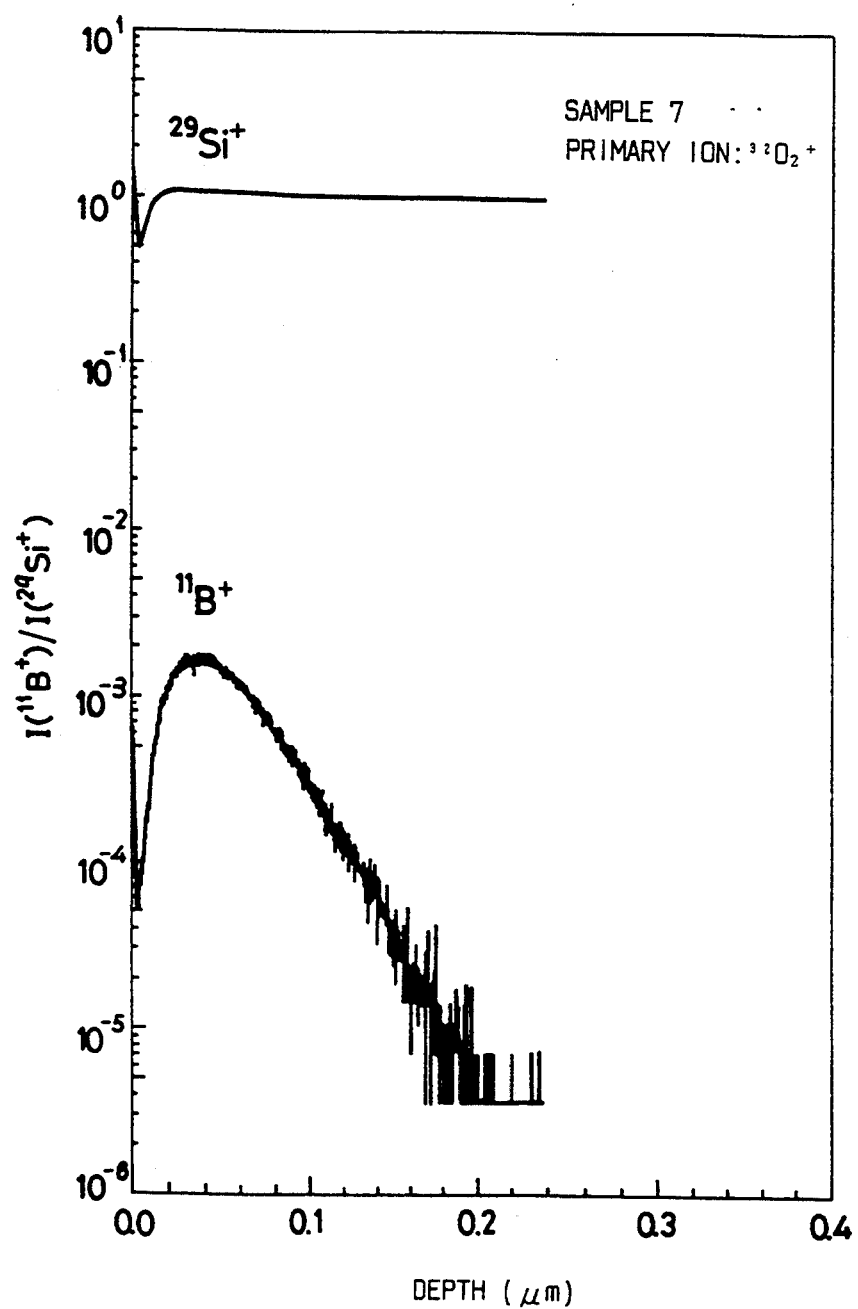
FIG. 10 is a graph showing a $^{11}B+/^{29}Si+$ relative secondary ion intensity distribution obtained by an SIMS analysis regarding a standard sample 7 in an embodiment of the invention.
Figure 11:
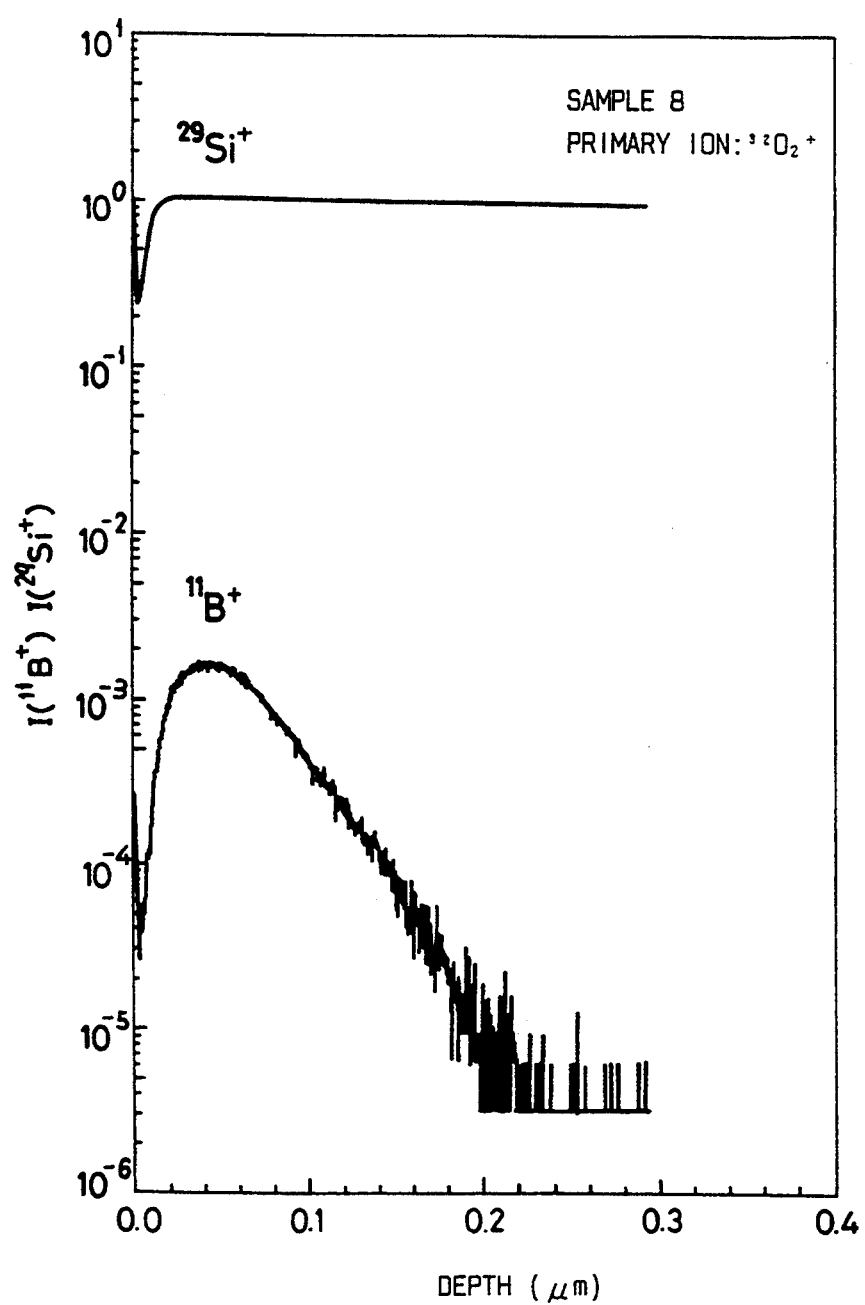
FIG. 11 is a graph showing a $^{11}B+/^{29}Si+$ relative secondary ion intensity distribution obtained by an SIMS analysis regarding a standard sample 8 in an embodiment of the invention.

It is now assumed that a depth at which $C_s$ reaches 99 % of the saturation concentration $K_0$ is set to a critical depth $D_x$. The dependencies of $D_x$ on the primary ion irradiation angle and the primary ion energy were examined. They are as shown in FIGS. 2 and 3, respectively. It will be understood from FIGS. 2 and 3 that the critical depth $D_x$ decreases as the irradiation angle increases and that $D_x$ increases with an increase in primary ion energy.

In the embodiment, a correction function of the secondary ion yield for a change in depth position in the region which is influenced by the primary ion implantation effect is derived. A quantitative correction is executed by correcting the actually measured secondary ion intensity by using the correction function, thereby performing the quantitative analysis. A method in this instance will now be sequentially explained hereinbelow.

In the following description, a region in which the uppermost layer of a sample having a contaminated layer due to a native oxide film, an adsorption of vapor, or the like exerts an influence on the SIMS depth profiling shape is called a region I. A deeper region in which an influence is exerted by the primary ion implantation effect is called a region II. A further deep region in which no influence is exerted any more by the primary ion implantation effect is called a region III.

In the embodiment, the correction function is derived by the following procedure. Consideration will now be first made with respect to the case of quantitatively analyzing B in the surface layer of an Si substrate. Consideration will be subsequently made with regard to the case of quantitatively analyzing As in the surface of the Si substrate.

Quantitative Analysis of B in the Surface Layer of the Si Substrate

First ions of $^{49}BF_2^+$ are implanted into an Si substrate by a dose of $1 \times 10^{13}/cm^2$ by using an implantation energy of 3.3 to 55 keV (0.74 to 12.35 keV) as an implantation energy of $^{11}B^+$), while changing the implantation energy at eight stages within such a range, thereby preparing standard samples 1 to 8, respectively. Preparing conditions of the standard samples 1 to 8 are shown in a lump in the following Table 1. The implantation energy is set by calculating from projected range data based on the LSS theory in a manner such that a depth of distribution peak of $^{11}B^+$ as implanted impurities, namely, the projected range $R_p$ is almost equal to the values shown in Table 1.

TABLE 1

| Sample No. | Sample Preparing Conditions | | Projected Range $R_p$ (nm) |
|---|---|---|---|
| | Implantation Energy (keV) | | |
| | $^{49}BF_2^+$ | $^{11}B^+$ | |
| 1 | 3.3 | 0.74 | 5 |
| 2 | 8 | 1.80 | 10 |
| 3 | 11 | 2.47 | 15 |
| 4 | 18 | 4.04 | 20 |
| 5 | 24 | 5.39 | 25 |
| 6 | 30 | 6.73 | 30 |
| 7 | 48 | 10.78 | 45 |
| 8 | 55 | 12.35 | 50 |

Subsequently, the optimum SIMS analyzing conditions are previously searched and the $^{11}B^+$ secondary ion intensity distributions of the standard samples 1 to 8 are measured under such conditions. In the SIMS analysis, the apparatus of ims-3F made by Cameca Co., Ltd. was used. In this apparatus, the irradiation angle $\theta$ of the primary ion is fixed to 30°.

The optimum SIMS analyzing conditions were determined by the preliminary experiments as shown by the following Table 2.

TABLE 2

| SIMS Analyzing Conditions | |
| --- | --- |
| Primary Ion Species | $^{32}O_2^+$ |
| Primary Ion Current ($I_P$) | 120 nA |
| Primary Ion Acceleration Voltage ($V_P$) | 15 kV |
| Raster Size ($L_R$) | 500 μm |
| Analyzing Region | 62 μmφ |
| Detected Ion Species/Polarity | $^{11}B^+$, $^{29}Si^+$ |

FIGS. 4 to 11 shows the results of the SIMS analyses which were executed with respect to the standard samples 1 to 8, respectively. Each of the graphs shows the depth dependency of the relative secondary ion intensity I ($^{11}B^+$)/I($^{29}Si^+$) of the $^{11}B^+$ secondary ion intensity I ($^{11}B^+$) to the $^{29}Si^+$ secondary ion intensity I ($^{29}Si^+$).

Figure 12:
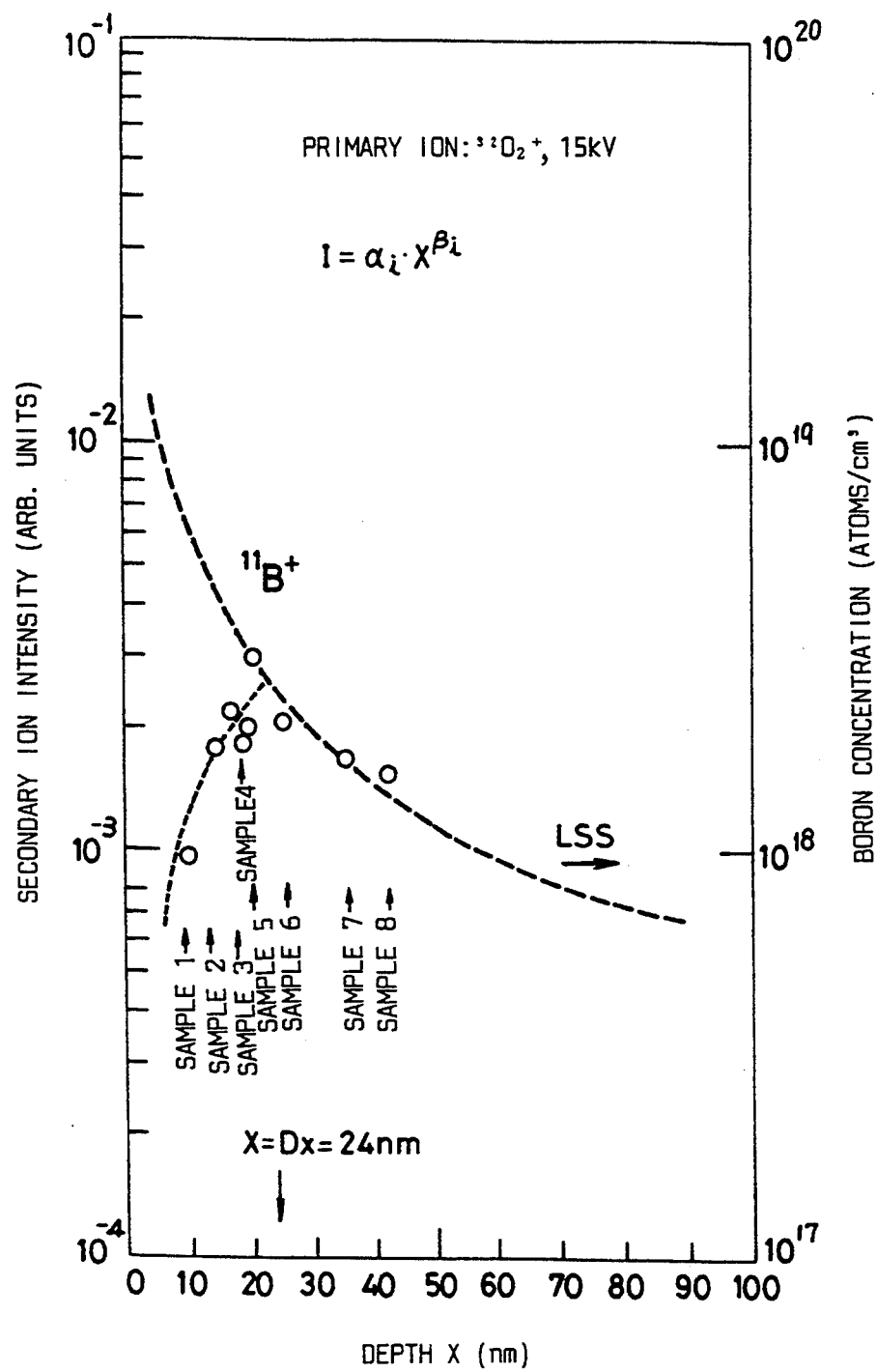
FIG. 12 is a graph showing a dependency of a $^{11}B+/^{29}Si+$ relative secondary ion intensity on a depth at a distribution peak point of B ion-implanted into the standard samples 1 to 8 in an embodiment of the invention.

In FIGS. 4 to 11, an attention is paid to the peak points corresponding to the projected range of the $^{11}B^+$ secondary ion intensity distribution and their appearance depth positions are obtained. The values of the secondary ion intensity (relative secondary ion intensity) I are plotted to those appearance depths (X) as shown in FIG. 12. An axis X of abscissa in FIG. 12 shows the depth which was measured from the interface between the regions I and II of the sample.

From FIG. 12, it will be understood that the I-X correlation causes a positive/negative inversion around the position of $X=D_x=24$ nm as a boundary. Namely, in the region of $X \leq D_x$, when X increases, I also increases. However, in the region of $X \geq D_x$, when X increases, I decreases.

An I-X plot curve of FIG. 12 is subsequently obtained as follows from the data of the secondary ion intensity I to each appearance depth at the peak points by a method of least square.

It is now assumed that a linear relation that is theoretically presumed is held between both of the logarithms of I and X. The following experimental equation (3) is obtained by the method of least square for each of the region ($X \leq D_x$) in which an influence is exerted by the primary ion implantation effect and the region ($X \geq D_x$) in which no influence is exerted by the primary ion implantation effect.

$$I = a_i \cdot X^{\beta_i} \ (i=1, 2) \tag{3}$$

Where i=1 and 2, which correspond to the region of X $\geq D_x$ and the region of $X \leq D_x$.

The value of $\alpha_i$ and $\beta_i$ in the equation (3) are shown in the following Table 3.

TABLE 3

| Values of $\alpha_i$ and $\beta_i$ in Each Region | | |
| --- | --- | --- |
| Region | $\alpha_i$ | $\beta_i$ |
| $X \leq D_x$ (i = 1) | $1.2 \times 10^{-4}$ | 0.96 |
| $X \geq D_x$ (i = 2) | $3.6 \times 10^{-2}$ | −0.86 |

When an attention is now paid to microvolumes ($\Delta V_1$, $\Delta V_2$) such that certain impurity elements have the same concentration ($C_1$, $C_2$) in the two regions (i=1, 2), the relations shown by the following equations (4), (5), and (6) are generally satisfied from the equation (3), respectively.

$$I_1 = a_1 \cdot X^{\beta_1} = k \cdot Y_1 \cdot C_1 \ (X \leq D_x) \tag{4}$$

$$I_2 = a_2 \cdot X^{\beta_2} = k \cdot Y_2 \cdot C_2 \ (X \geq D_x) \tag{5}$$

$$C_1 = C_2 \tag{6}$$

Here, $Y_1$ and $Y_2$ denote secondary ion yields in the region i=1 and the region i=2.

In the region shown by i=1, namely, in the region II, a secondary ion yield Y changes as a function of X by being influenced by the primary ion implantation effect, so that it is regarded that a secondary ion current also changes as a function of the depth X.

In consideration of the above points, when $Y_1 = Y_R Y$ ($X \leq D_x$) and $Y_2 = Y$ ($X \geq D_x$) are set, the following equation (7) is obtained from the equations (4), (5), and (6).

$$Y_R(X) = Y_1(X)/Y_2(X) = (\alpha_1/\alpha_2) X^{\beta_1 - \beta_2} \tag{7}$$

Further, when $X = D_x$, $I_1(D_x) = I_2(D_x)$, so that $Y_1(D_x) = Y_2(D_x)$. Thus, $Y_R(D_x) = 1$.

Figure 13:
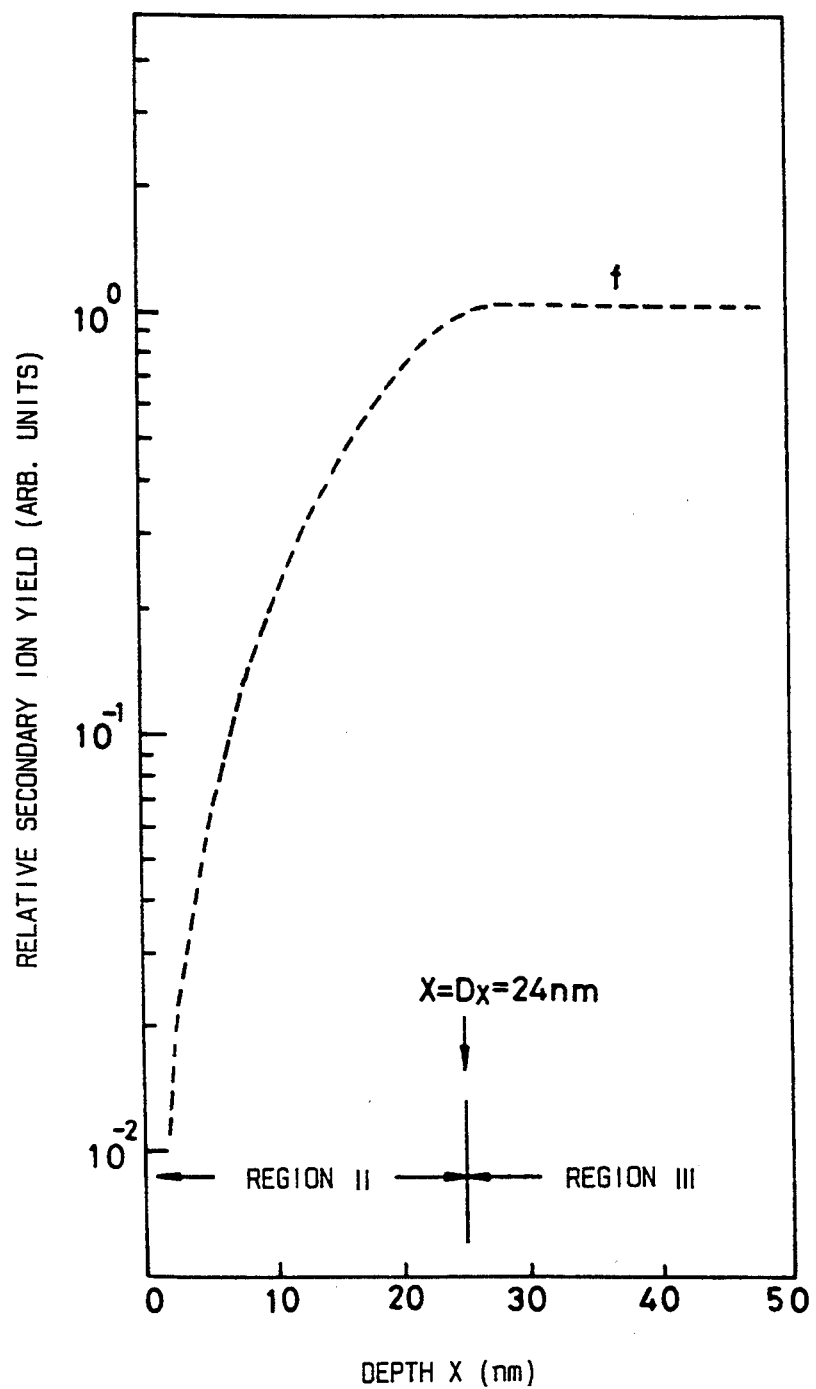
FIG. 13 is a graph showing a correction function of a secondary ion yield obtained in an embodiment of the invention.

Now, assuming that $$\begin{aligned} f(X) &= Y_R(X)/Y_R(D_x) \\ &= \frac{(\alpha_1/\alpha_2) X^{\beta_1 - \beta_2}}{(\alpha_1/\alpha_2) D_x^{\beta_1 - \beta_2}} \\ &= (X/D_x)^{\beta_1 - \beta_2} \end{aligned} \tag{8}$$

the equation (8) shows a change in secondary ion yield case of $X \leq D_x$. That is, the secondary ion yield in the region II changes in accordance with a function f(X) that is expressed by the equation (8) for a period of time until the concentration of oxygen as primary ion species is saturated in the sample substrate. The relations of f(X) - X are now plotted by using the experimental values in the Table 3 as shown in FIG. 13.

f(X) shown in the equation (8) and FIG. 13 denotes a correction function. By using the correction function f(X) derived as mentioned above, a secondary ion intensity $I_{exp}(X)$ which has actually been measured in the region I in which an influence is exerted by the primary ion implantation effect is corrected by using the following equation (9), so that a secondary ion intensity $I_{corr}$ corrected as mentioned above can be obtained.

$$\begin{aligned} I_{corr} &= f(X)^{-1} \cdot I_{exp}(X) \\ &= (X/D_x)^{-(\beta_1 - \beta_2)} \cdot I_{exp}(X) \end{aligned} \tag{9}$$

Explanation will now be made with respect to a method whereby the secondary ion intensity distribution of B which has actually been obtained in the ultrashallow region is corrected by using the correction function f(X) derived as mentioned above and B is quantitatively analyzed.

As evaluation samples, the following two kinds of samples were used: namely, a sample (sample A) in which an SiO$_2$ film having a thickness of 8 nm was formed onto an Si substrate and ions of $BF_2{}^+$ were implanted into such an Si substrate by a dose of $3 \times 10^{15}/cm^2$ by using an implantation energy 15 keV; and a sample (sample B) which is obtained by further executing a pre-annealing process at 550° C. for one hour to the sample A and by subsequently performing a laser annealing at an energy density of 870 $mJ/cm^2$ for 20 sec by using an excimer laser.

A concentration distribution (broken line) of B in the depth direction after completion of the execution of the quantitative correction is overwritten together with that (solid line) before the correction to the concentration distribution of B obtained by executing the SIMS analysis with respect to the samples A and B. The result is show in FIG. 14.

Figure 14:
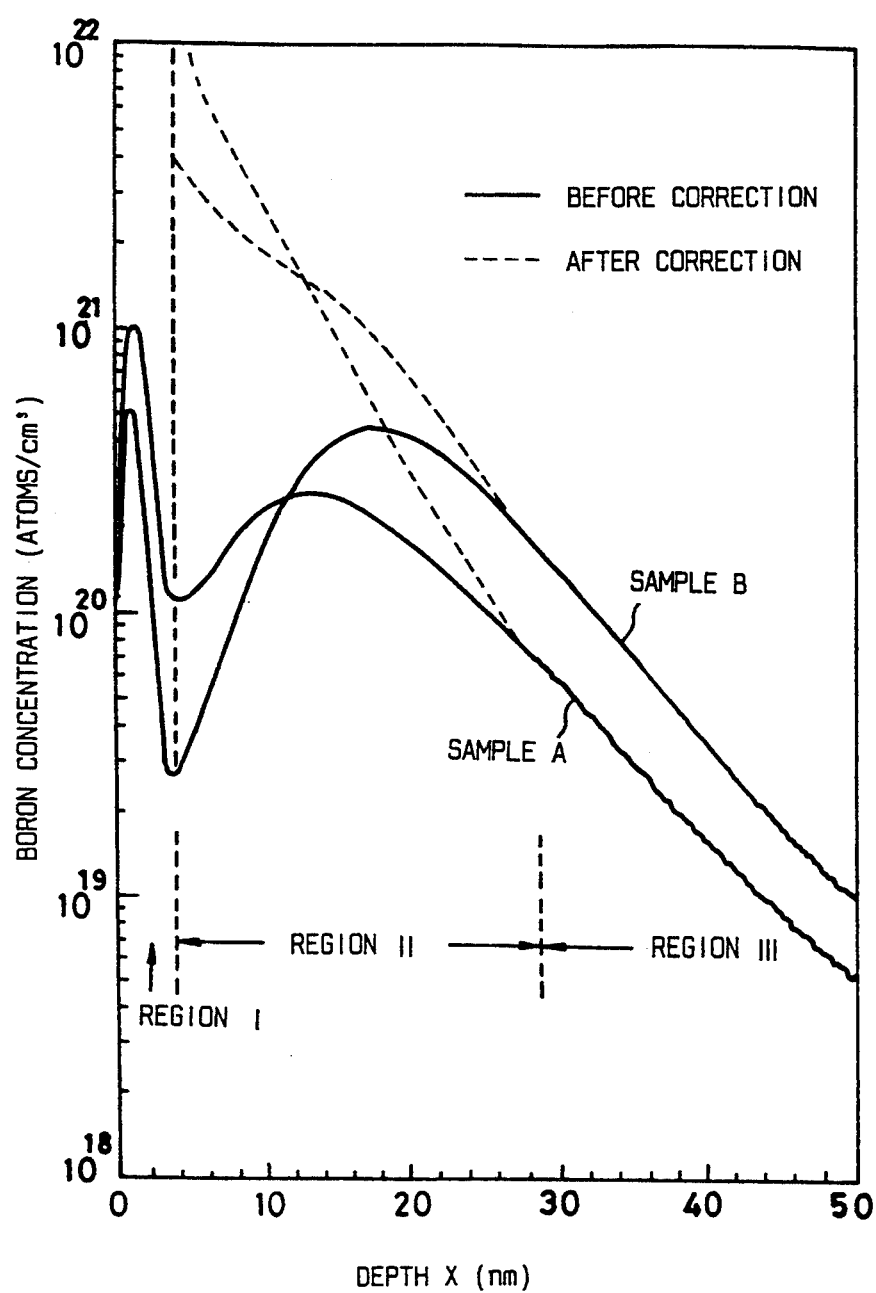
FIG. 14 is a graph showing an example of B concentration distributions before and after the quantitative correction using the correction function shown in FIG. 13.

In FIG. 14, when the B concentration distribution curve before correction is seen, an apparent peak of the B concentration distribution appears at the position of X=13.0 nm with respect to the sample A and at the portion of X=17.5 nm with regard to the sample B. However, when considering the thickness of $SiO_2$ film formed on t Si substrate, the peak position of the B concentration distribution which is presumed in the sample A is away from the surface of the Si substrate by a distance of about 3.6 nm. Therefore, such a peak position can appear at a position that is shallower by up to 10 nm from the peak position of the concentration distribution of B in FIG. 14. It will be understood from the above viewpoint that the peak point appearing in FIG. 14 does not reflect the peak of the actual B concentration distribution.

On the other hand, in FIG. 14, when the concentration distribution of B after the quantitative correction was performed by using the correction function f(X) is seen, the peaks seen in the concentration distribution before correction do not appear in both of the samples A and B and it will be understood that the concentration monotonously decreases with an increase in X. In this case, as for the sample B to which the annealing process was executed, a concentration decreases on the shallow side of the region II in which an influence is exerted by the primary ion implantation effect, and on the contrary, a distribution of a higher concentration is obtained on the deep side. In the deep region III, it will be understood that the concentration of B in case of the sample B which was annealed is higher than that of the sample A which was not annealed. From this point, a situation such that a redistribution of B occurs due to a diffusion of B by annealing can be clearly understood.

As mentioned above, by executing the quantitative correction by using the correction function f(X), an explanation will be easily given to a point which is difficult to understood in the concentration distribution before correction.

Figure 15:
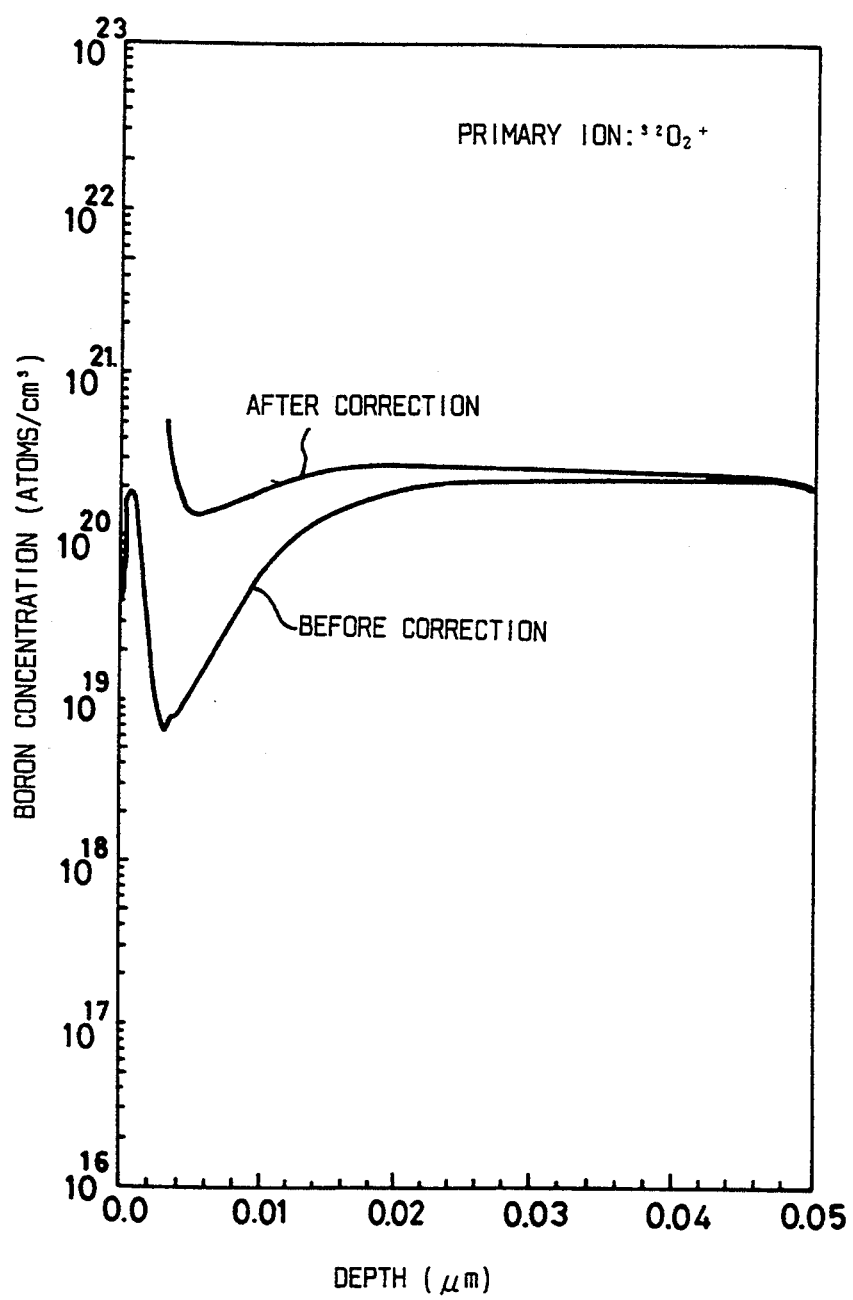
FIG. 15 is a graph showing another example of B concentration distributions before and after the quantitative correction using the correction function shown in FIG. 13.
Figure 16:
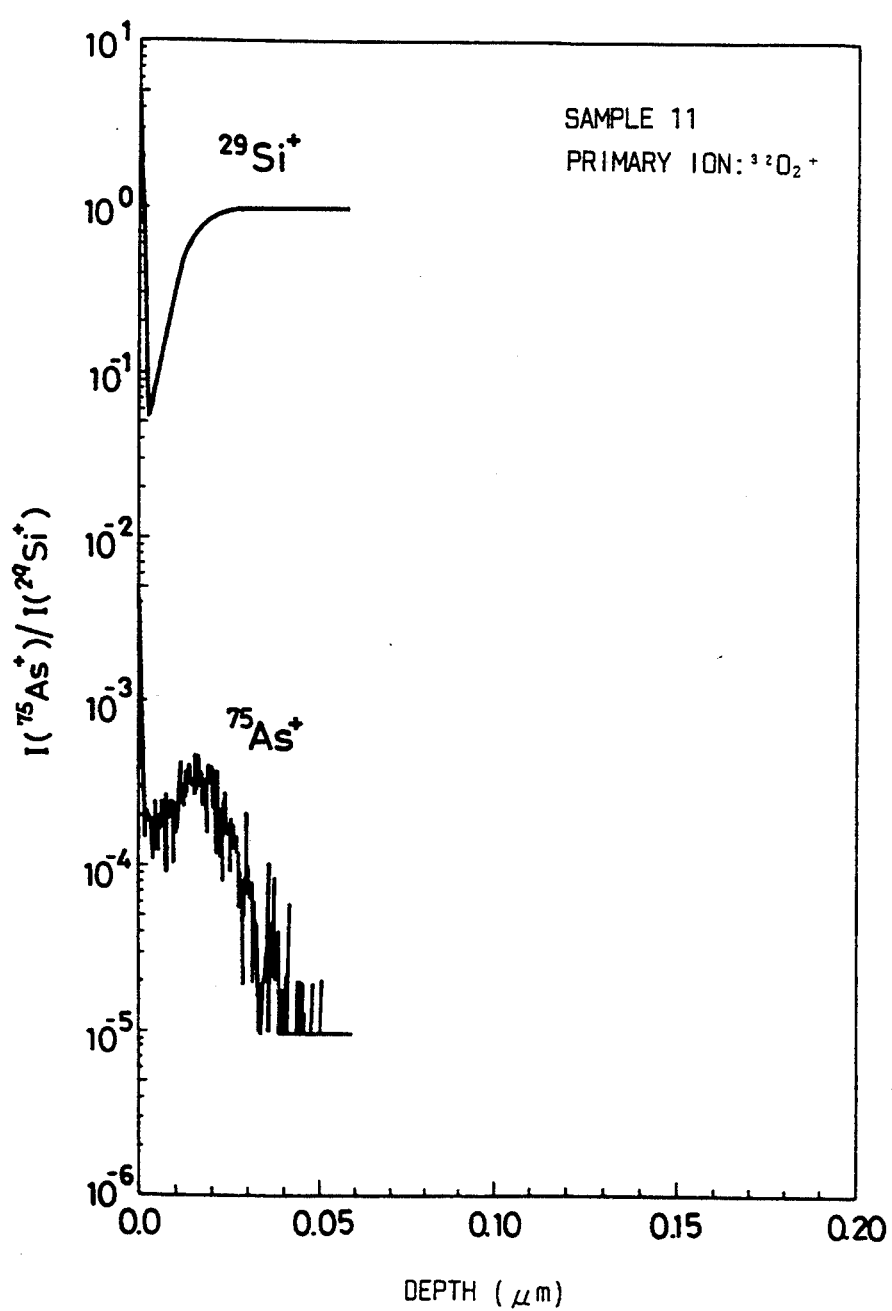
FIG. 16 is a graph showing a $^{75}As+/^{29}Si +$ relative secondary ion intensity distribution obtained by an SIMS analysis regarding a standard sample 11 in an embodiment of the invention.
Figure 17:
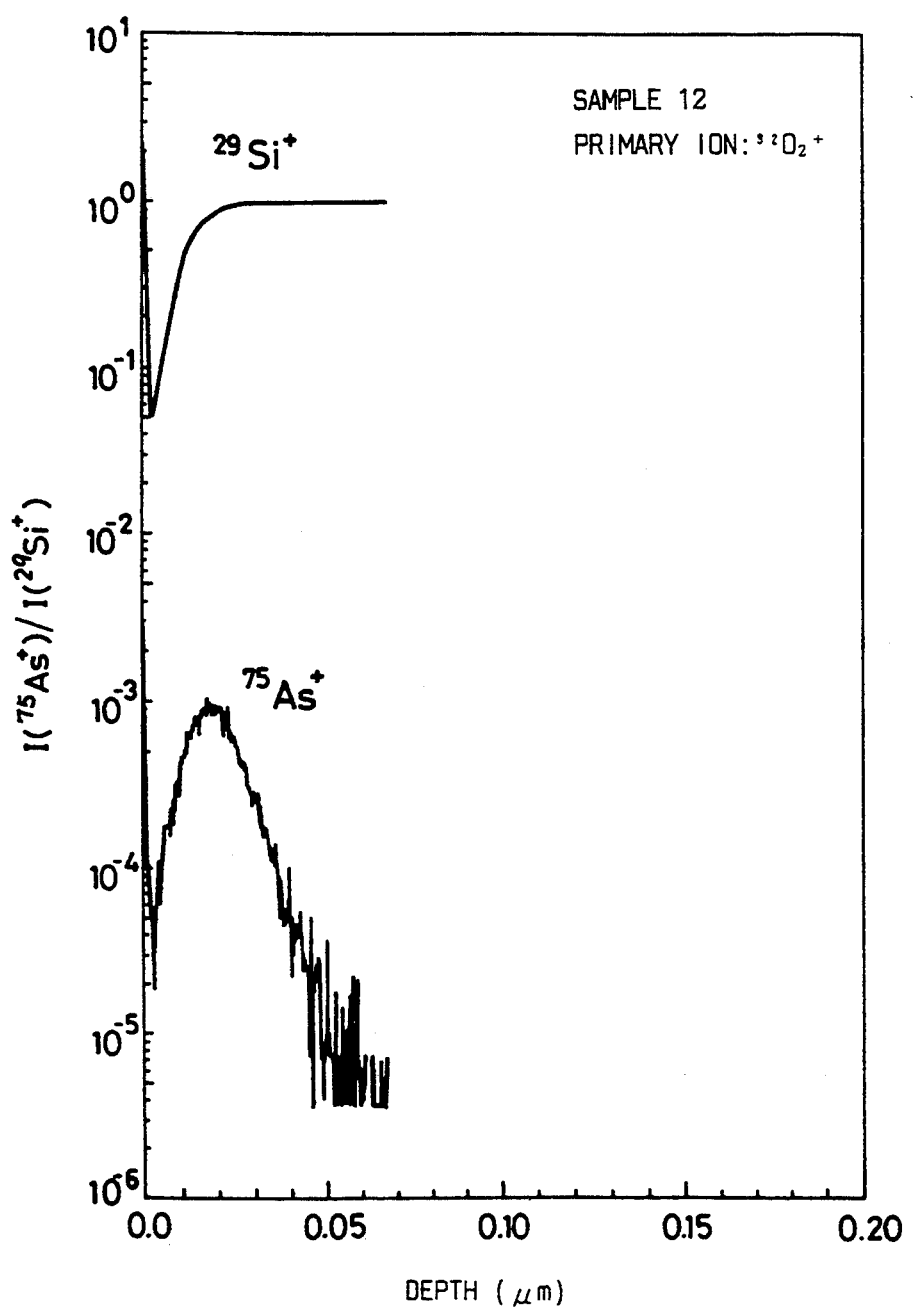
FIG. 17 is a graph showing a $^{75}As+/^{29}Si +$ relative secondary ion intensity distribution obtained by an SIMS analysis regarding a standard sample 12 in an embodiment of the invention.
Figure 18:
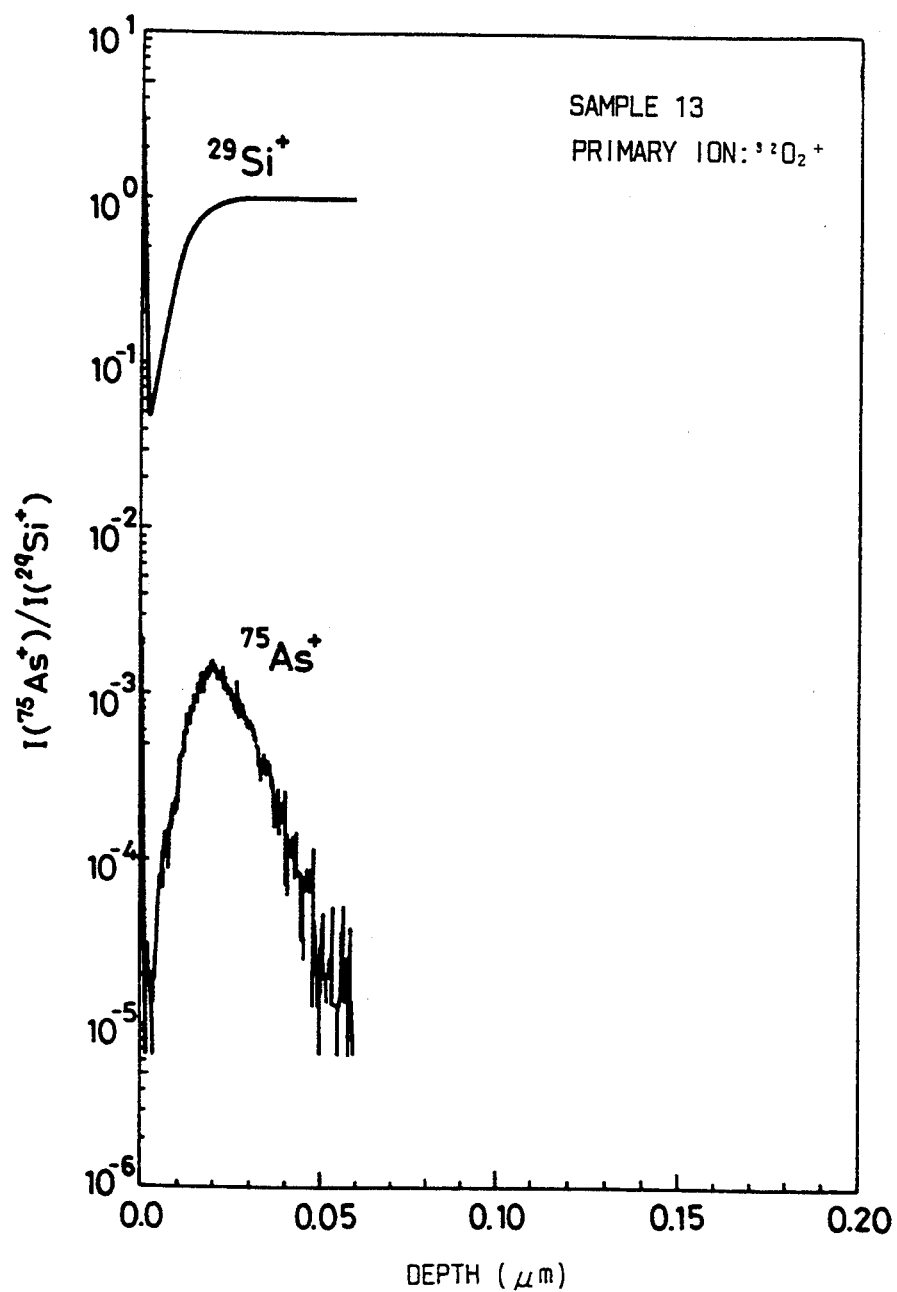
FIG. 18 is a graph showing a $^{75}As+/^{29}Si +$ relative secondary ion intensity distribution obtained by an SIMS analysis regarding a standard sample 13 in an embodiment of the invention.
Figure 19:
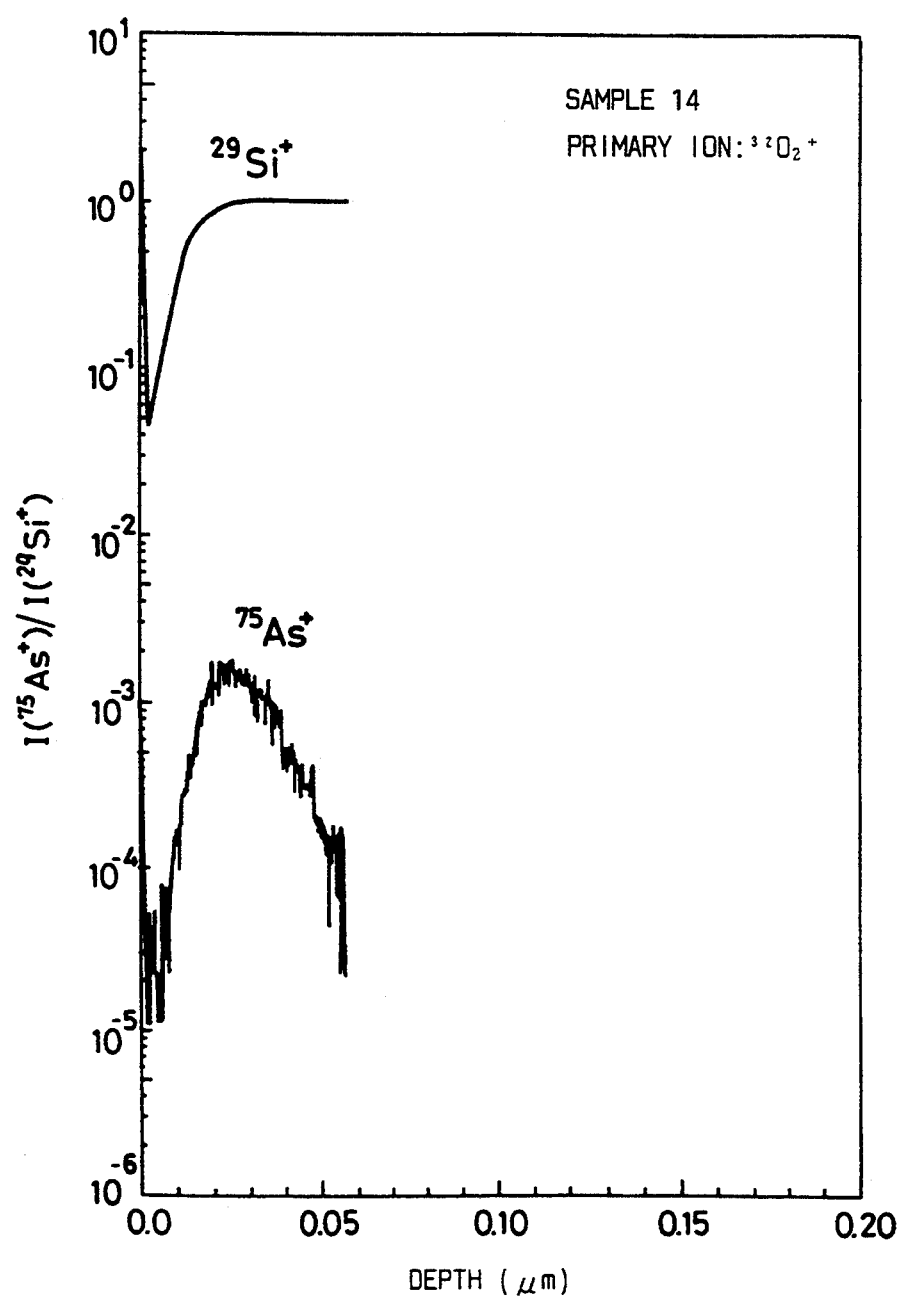
FIG. 19 is a graph showing a $^{75}As+/^{29}Si +$ relative secondary ion intensity distribution obtained by an SIMS analysis regarding a standard sample 14 in an embodiment of the invention.
Figure 20:
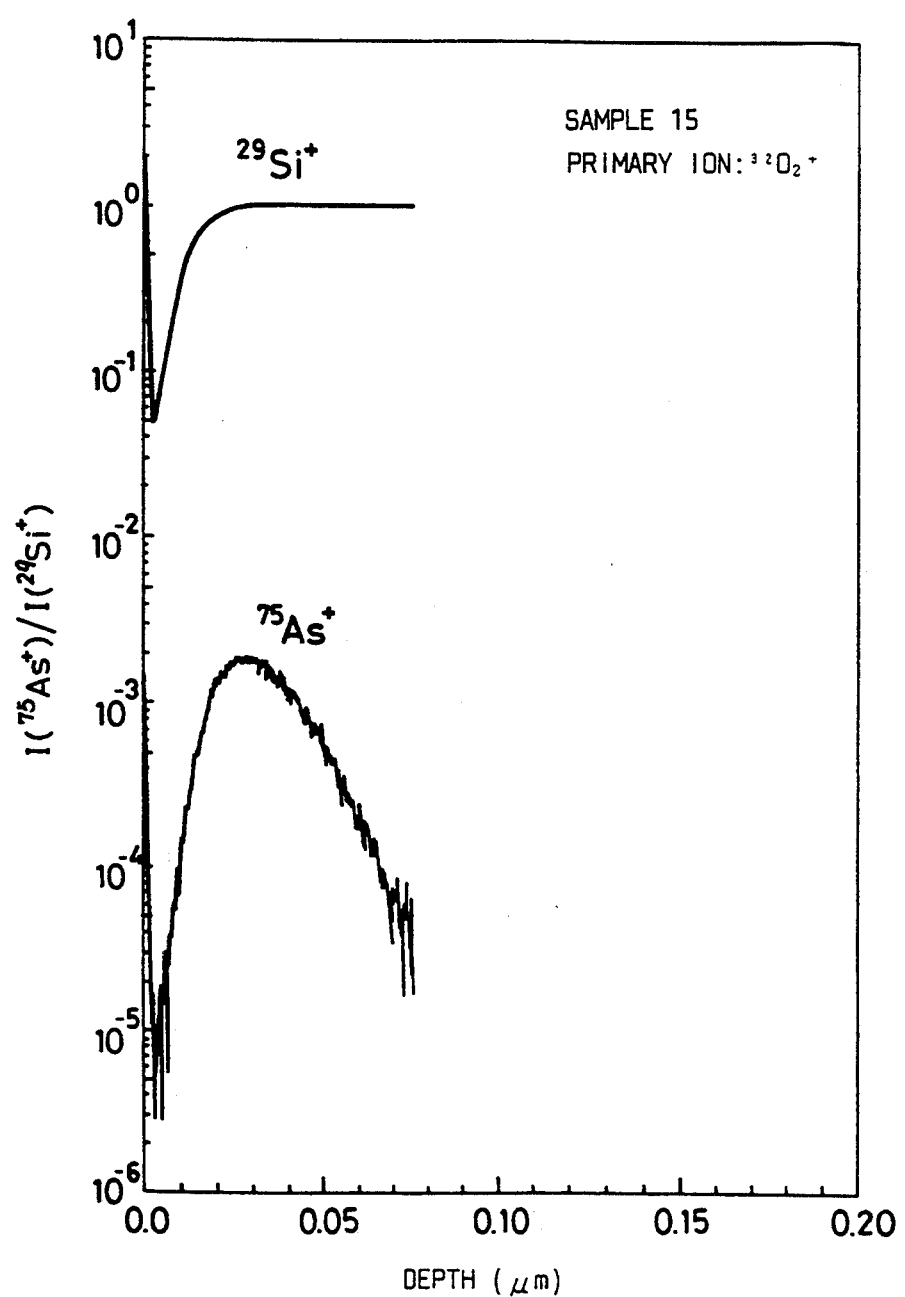
FIG. 20 is a graph showing a $^{75}As+/^{29}Si +$ relative secondary ion intensity distribution obtained by an SIMS analysis regarding a standard sample 15 in an embodiment of the invention.
Figure 21:
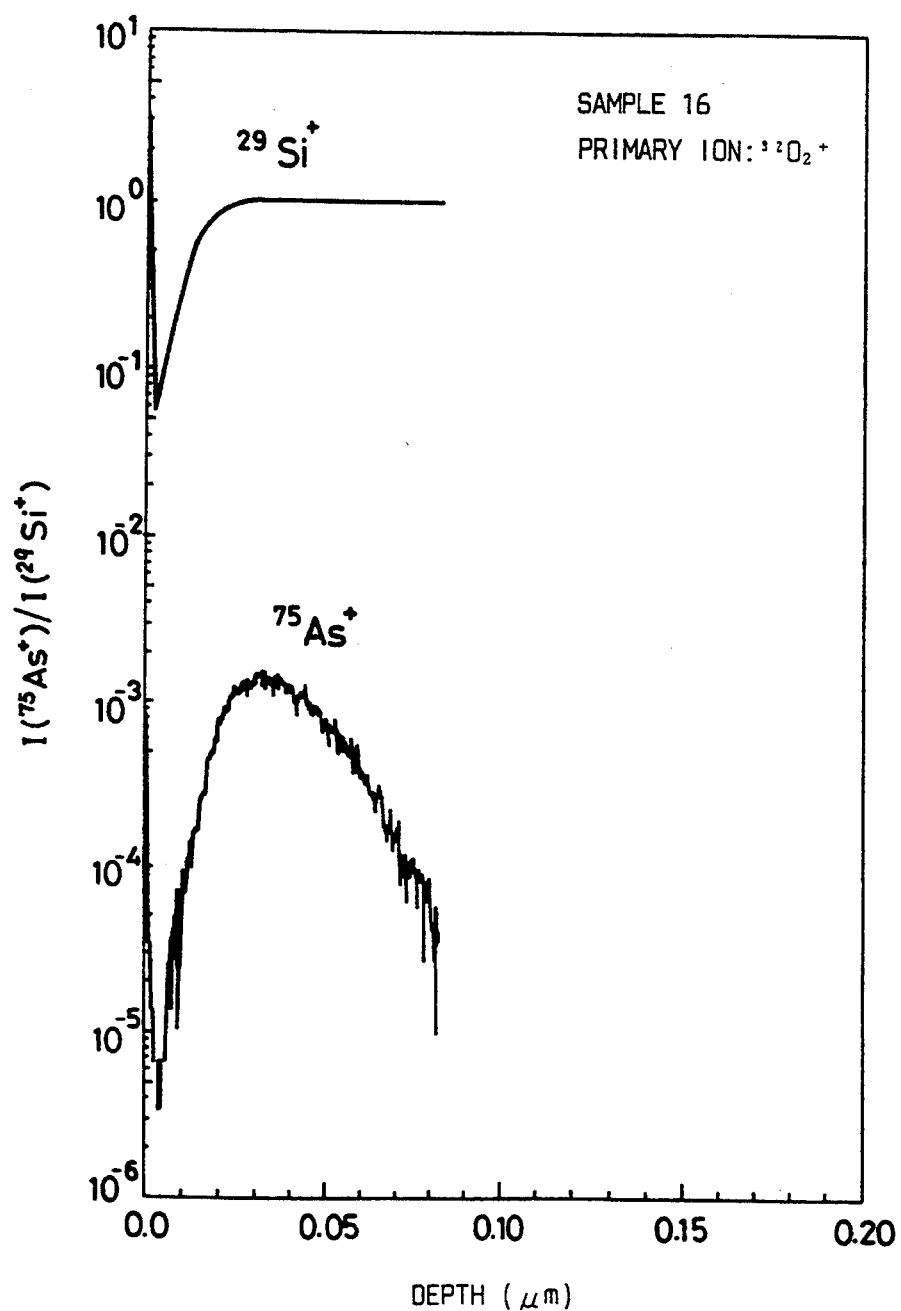
FIG. 21 is a graph showing a $^{75}As+/^{29}Si +$ relative secondary ion intensity distribution obtained by an SIMS analysis regarding a standard sample 16 in an embodiment of the invention.
Figure 22:
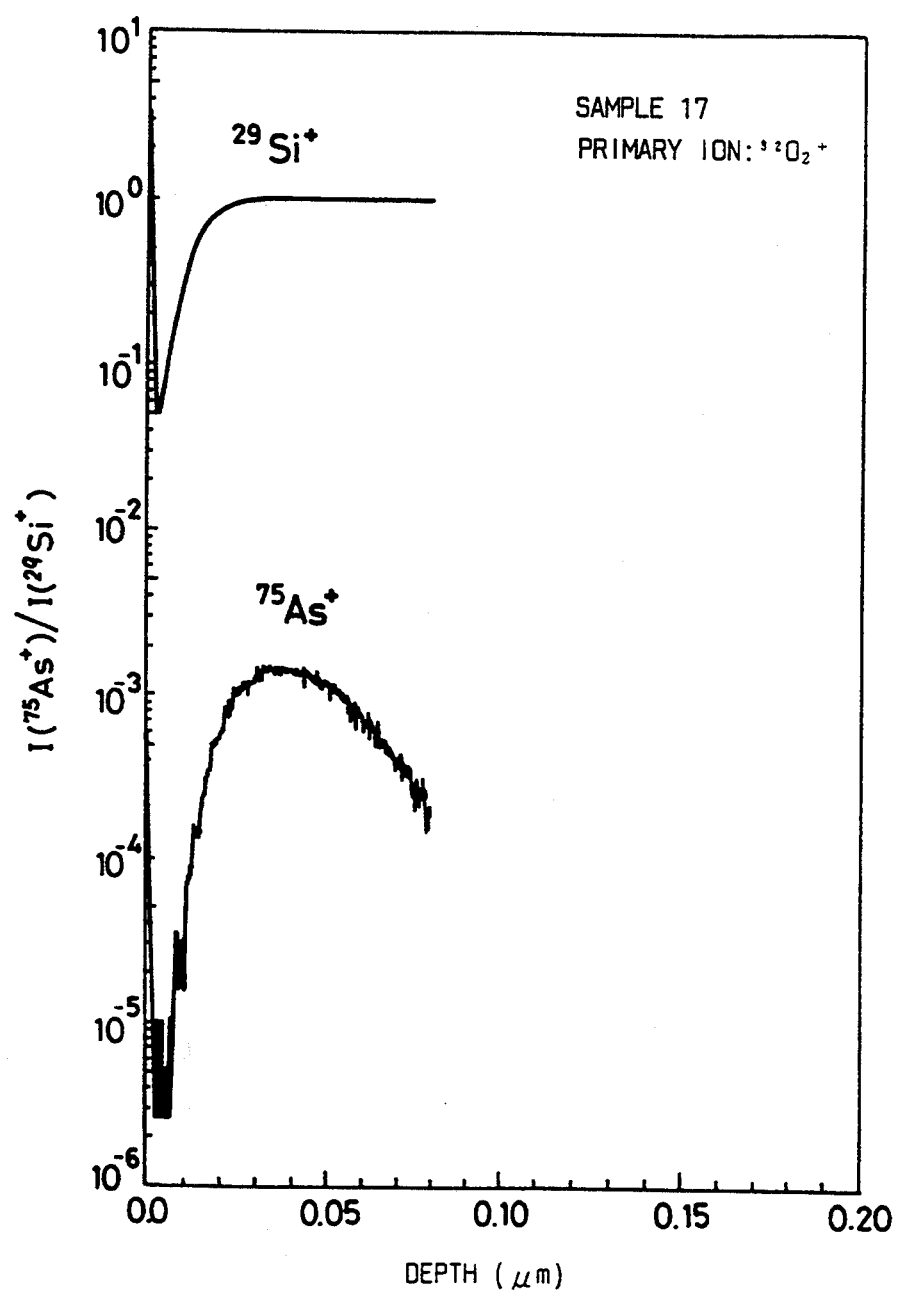
FIG. 22 is a graph showing a $^{75}As+/^{29}Si +$ relative secondary ion intensity distribution obtained by an SIMS analysis regarding a standard sample 17 in an embodiment of the invention.
Figure 23:
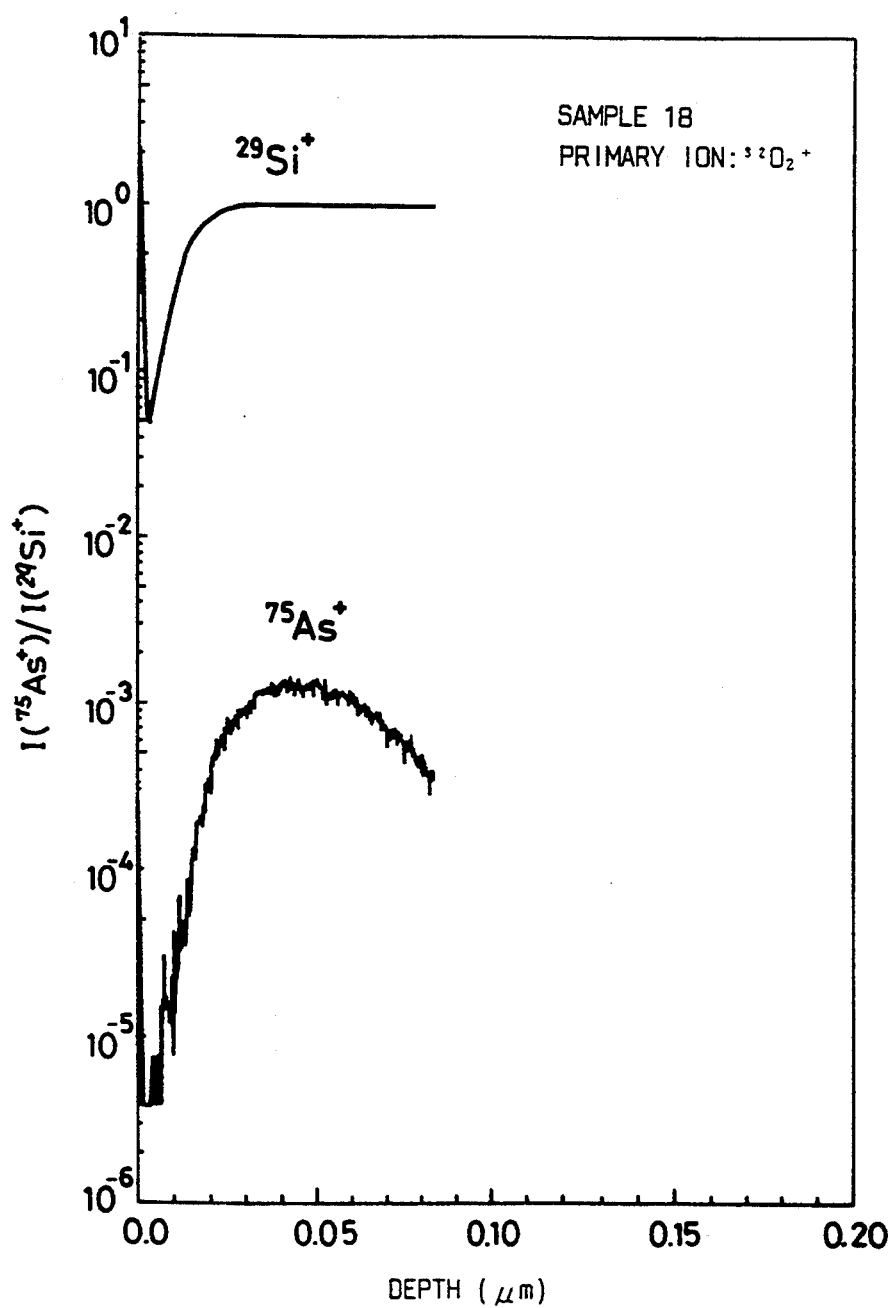
FIG. 23 is a graph showing a $^{75}As+/^{29}Si +$ relative secondary ion intensity distribution obtained an SIMS analysis regarding a standard sample 18 in an embodiment of the invention.
Figure 24:
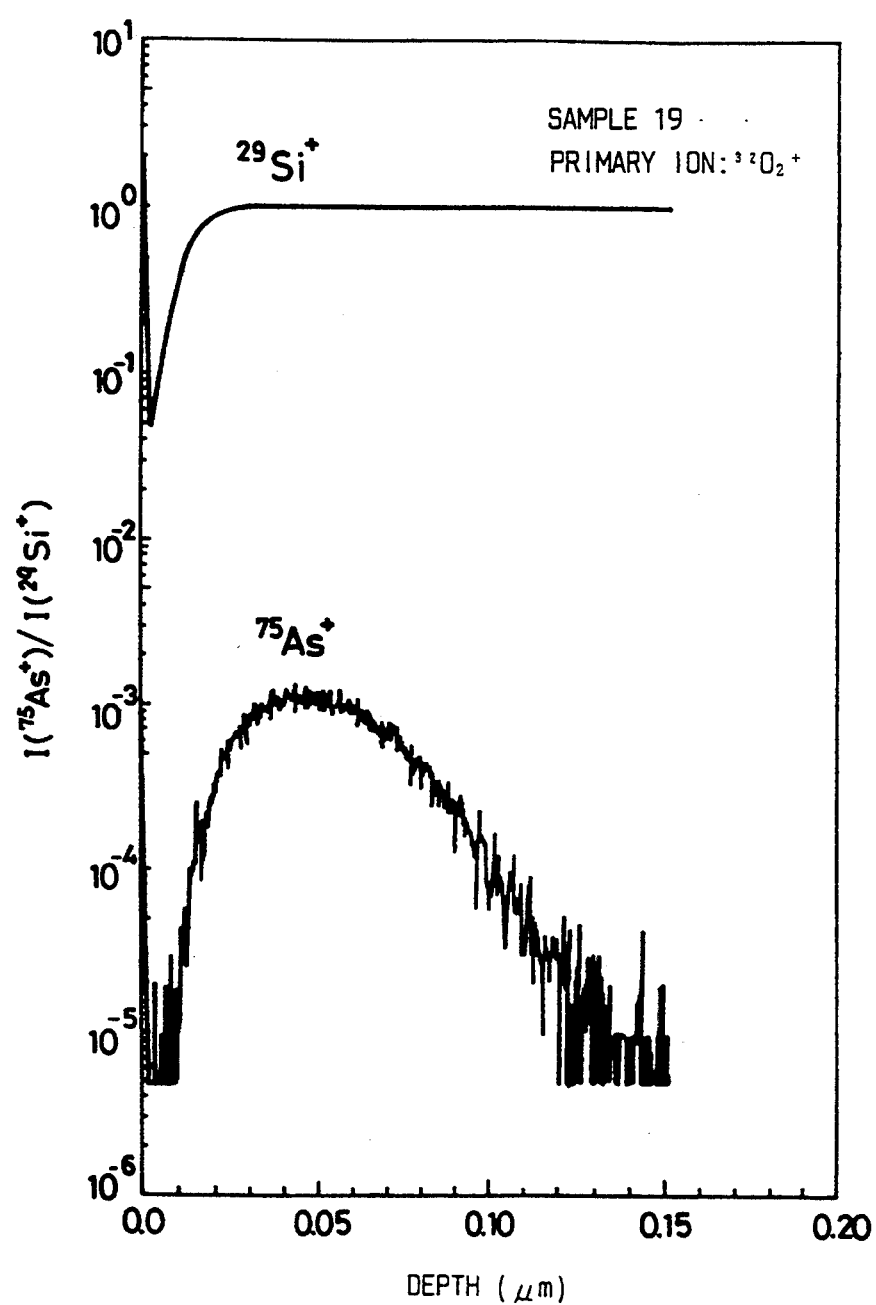
FIG. 24 is a graph showing a $^{75}As+/^{29}Si +$ relative secondary ion intensity distribution obtained by an SIMS analysis regarding a standard sample 19 in an embodiment of the invention.

FIG. 15 shows another example of concentration distributions before and after the quantitative correction.

Quantitative Analysis of As in the Surface Layer of the Si Substrate

First, $^{75}As^+$ ions were implanted into an Si substrate by a dose of $4.1 \times 10^{14}/cm^2$ by using an implantation energy in a range of 3.9 to 75 keV, while changing the implantation energy to nine stages within such a range, thereby preparing standard samples 11 to 19. Preparing conditions of each of the standard samples 11 to 19 are shown in a lump in the following Table 4. The implantation energy was set by calculating from the projected range data based on the LSS theory in a manner such that the depth of distribution peak of $^{75}As^+$ as implanted impurities, namely, the projected range $R_P$ is almost equal to the values as shown in the Table 4 in a manner similar to the case of the quantitative analysis of B mentioned above.

TABLE 4

| | Preparing Conditions of Samples | | |
|---|---|---|---|
| Sample No. | Implantation Energy (keV) | Projected Range $R_P$ (nm) | Peak Concentration (atoms/cm$^3$) |
| 11 | 3.87 | 5 | 8.59 × 10$^{20}$ |
| 12 | 10.50 | 10 | 4.36 × 10$^{20}$ |
| 13 | 18.50 | 15 | 2.91 × 10$^{20}$ |
| 14 | 27.50 | 20 | 2.17 × 10$^{20}$ |
| 15 | 36.50 | 25 | 1.75 × 10$^{20}$ |
| 16 | 45.00 | 30 | 1.50 × 10$^{20}$ |
| 17 | 55.00 | 35 | 1.27 × 10$^{20}$ |
| 18 | 65.00 | 40 | 1.12 × 10$^{20}$ |
| 19 | 75.00 | 45 | 1.00 × 10$^{20}$ |

In a manner similar to the case of the quantitative analysis of B, the $^{75}As^+$ secondary ion intensity distributions of the standard samples 11 to 19 were measured under the optimum SIMS analyzing conditions which have previously been searched. In the SIMS analysis, the apparatus of ims-4F made by Cameca Co., Ltd. was used. The optimum SIMS analyzing conditions were determined by the preliminary experiments as shown in following Table 5.

TABLE 5

| SIMS Analyzing Conditions | |
|---|---|
| Primary Ion Species | $^{32}O_2{}^+$ |
| Primary Ion Current ($I_P$) | 140 nA |
| Primary Ion Acceleration Voltage ($V_P$) | 15 kV |
| Raster Size ($L_R$) | 500 μm |
| Analyzing Region | 62 μmφ |
| Detected Ion Species/Polarity | $^{75}As^+$, $^{29}Si^+$ |
| Analyzing Mode | Energy Offset Mode (Offset Voltage: 60V) |

Although the analyzing condition shown in Table 5 are substantially the same as the analyzing conditions in case of the quantitative analysis of B, in this case, in order to eliminate the influence by ($^{29}Si^{30}Si + ^{16}O+$) as interference ions for $^{75}As^+$, an energy offset mode (offset voltage: 60 V) was used as an analyzing mode of the secondary ion.

FIGS. 16 to 24 show the results of the SIMS analyses which were executed with respect to the standard samples 11 to 19, respectively. Each of the graphs shows a depth dependency of the relative secondary ion intensity $I(^{75}As^+)I(^{29}Si^+)$ of the $^{75}As^+$ secondary ion intensity $I(^{75}As^+)$ to the $^{29}Si^+$ secondary ion intensity $I^{29}Si^+$).

Figure 25:
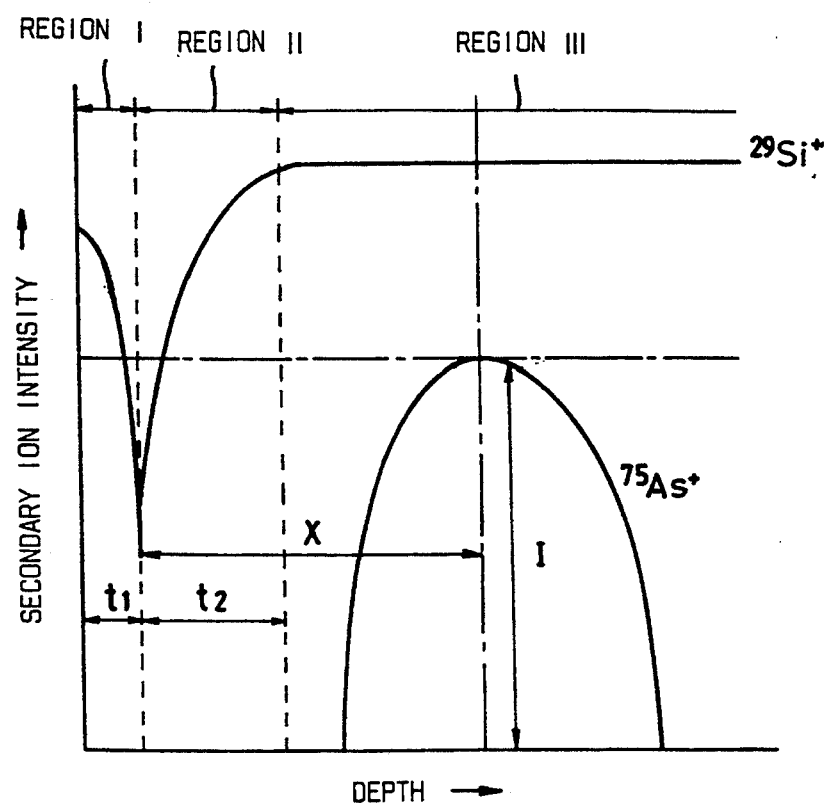
FIG. 25 is a graph showing definitions of widths ($t_1$, $t_2$) of areas I and II, a peak depth X of the distribution, and a relative secondary ion intensity I corresponding thereto which were measured with respect each of the standard samples 11 to 19.

In FIGS. 16 to 24, the region was divided into the regions I, II, and III. The following Table 6 shows the results of the measurements of the widths ($t_1$, $t_2$) of the regions I and II, peak depth X of the $^{75}As^+$ secondary ion intensity distribution, and relative secondary ion intensity I. $t_2$ denotes a width from the interface between the regions I and II to the position at which the $^{29}Si^+$ secondary ion intensity reaches 84.13% of its saturation value. FIG. 25 shows the definitions of $t_1$, $t_2$, X and I.

TABLE 6

Actual Measure Widths of the Regions I and II,
Peak Depth X, and Relative Secondary Ion Intensity I

| Sample No. | Region I $t_1$ (nm) | Region II $t_2$ (nm) | X (nm) | I ($\times 10^3$) |
|---|---|---|---|---|
| 11 | 3.3 | 19.0 | 12.4 | 0.3 |
| 12 | 2.6 | 18.0 | 16.0 | 0.9 |
| 13 | 2.5 | 18.0 | 17.5 | 1.4 |
| 14 | 2.6 | 18.0 | 21.7 | 1.5 |
| 15 | 2.8 | 18.0 | 24.3 | 1.9 |
| 16 | 2.8 | 18.0 | 28.4 | 1.5 |
| 17 | 2.7 | 18.0 | 33.0 | 1.4 |
| 18 | 2.8 | 19.0 | 40.1 | 1.3 |
| 19 | 2.5 | 17.0 | 43.2 | 1.1 |

Figure 26:
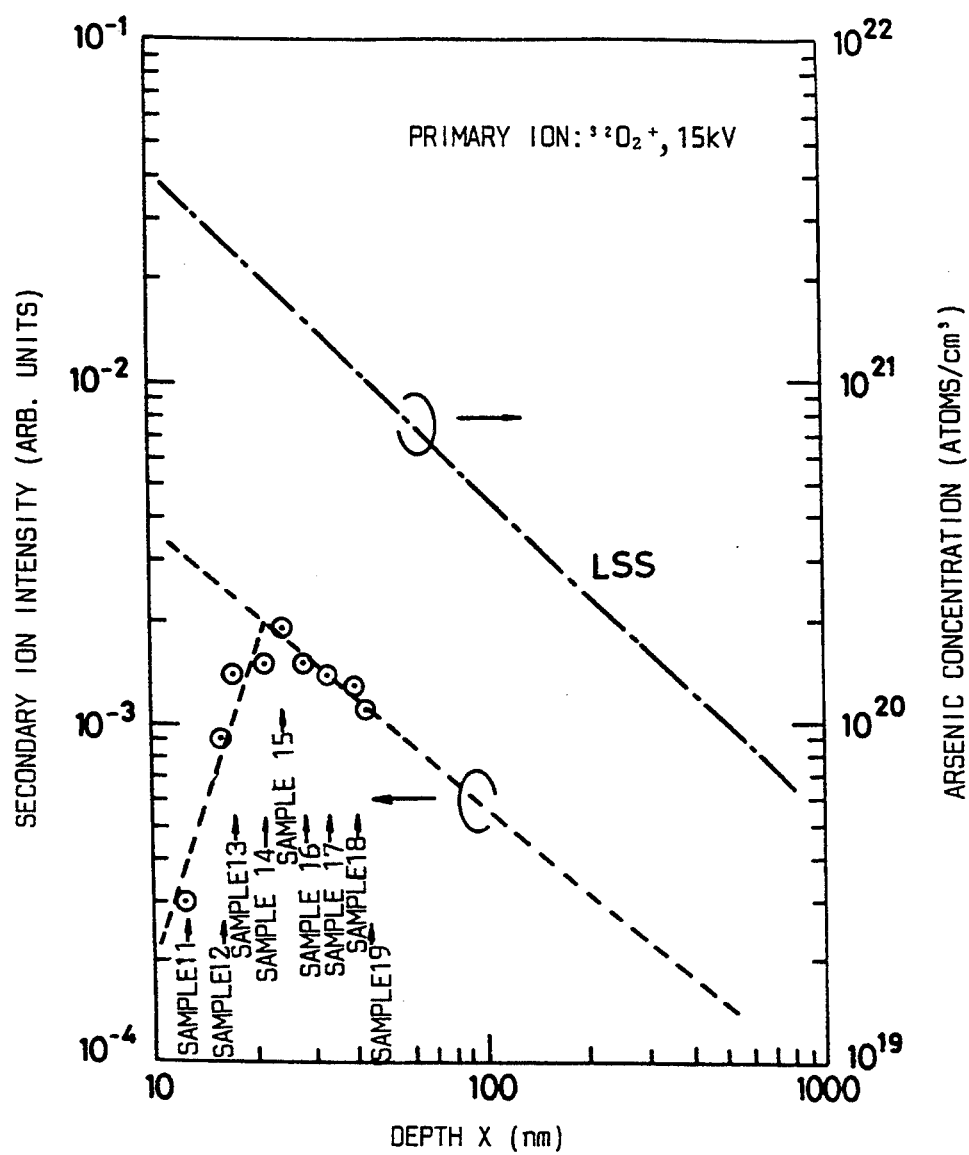
FIG. 26 is a graph showing a dependency of the $^{75}As^+/^{28}Si^+$ relative secondary ion intensity on a depth at a distribution peak point of As ion-implanted into each of the standard samples 11 to 19 in an embodiment of the invention.

The values of I are plotted to X from the measured values in Table 6, so that the results as shown in FIG. 26 are obtained. The existence of the I-X correlation will be obviously seen. That is, as the implantation energy of $^{75}As^+$ decreases within a range from 36.5 to 75 keV (standard samples 15 to 19), X also decreases and I increases. Such a tendency coincides with a tendency that is theoretically presumed. However, it will be obviously understood that X decreases from a location of the implantation energy near 27.5 to 36.5 keV (peak depth is about 24.3 to 27.1 nm) (standard samples 14 and 15) as a boundary, but I exits a decreasing tendency opposite to the tendency that is theoretically presumed. The peak value of the As concentration distribution which is presumed from the LSS theory is plotted to the projected range which is determined by the implantation energy. The result which is obtained by such plotting is shown by an alternate long and short dash line in FIG. 26.

From the actually measured distribution characteristics and the presumed distribution characteristics as mentioned above, it will be obviously understood that in case of the standard samples 11 to 14 in which the implantation energy is low ($3.9 \leq E \leq 27.5$ to 36.5 keV), the relative secondary ion intensity I of the sample of a smaller implantation energy (shallower peak depth) does not reflect the true concentration value of As.

From the data of the relative secondary ion intensity I for each peak depth X in Table 6, an I-X plotting curve is obtained by the method of least square in a manner similar to the case of the quantitative analysis of B. In this case, the values of $\alpha_i$ and $\beta_i$ in the equation (3) are as shown in the following Table 7.

TABLE 7

Values of $\alpha_i$ and $\beta_i$ in Each Region

| Region | $\alpha_i$ | $\beta_i$ |
|---|---|---|
| $X \leq D_x$ (i = 1) | $2.00 \times 10^{-7}$ | 3.00 |
| $X \geq D_x$ (i = 2) | $2.40 \times 10^{-2}$ | −0.81 | f(X) is obtained from the equation (8) by using the experimental values in Table 7 and the secondary ion intensity $I_{corr}$ which was corrected by the equation (9) can be obtained by using f(X).

Examination of Correcting Equations

As mentioned above, a change in secondary ion yield in the region (region II) in which an influence is exerted by the primary ion implantation effect is expressed by the equation (8). $D_x$ in the equation (8) denotes the depth until the concentration of the primary ion species which was irradiated upon analysis, namely, oxygen is saturated in the substrate. Therefore, it will be obviously understood that $D_x$ depends on the setting conditions of the primary ion.

As will be obviously understood from FIG. 26 the exponent $(\beta_1-\beta_2)$ in the equation (8), $\beta_2$ indicates a change in secondary ion intensity in the region (region III) in which no influence is exerted the primary ion implantation effect. The secondary ion yield in the region III assumes constant. On the other hand, $\beta_1$ denotes a change in secondary ion intensity, namely, a change in secondary ion yield in the region (region II) in which an influence is exerted by the primary ion implantation effect.

From the above viewpoint, it will be obviously understood that the exponent in the equation (8) is directly concerned with the secondary ion yield.

On the other hand, it has already been known that the secondary ion yield differs depending on an element. Therefore, since the portion which depends on the element is the exponent in the equation (8), it is presumed that by clarifying the relation between the value of the exponent and the element, a general correcting equation which can be applied to various kinds of elements can be derived.

Therefore, the value of the exponent in the equation (8) obtained by the experiments in case of the quantitative analysis of B mentioned above was compared with the value of the exponent in the equation (8) obtained by the experiments in case of the quantitative analysis of As. The value of $\beta_1$ and $\beta_2$ indicative of the changes of the secondary ion yields obtained from the results of the experiments and the values of $(\beta_1-\beta_2)$ are shown in the following Table 8.

TABLE 8

Factors Showing a Change in Secondary Ion Yield

| Element | $\beta_1$ | $\beta_2$ | $\beta_1-\beta_2$ |
|---|---|---|---|
| B | 0.96 | −0.86 | 1.82 |
| As | 3.00 | −0.81 | 3.81 |

It will be understood from Table 8 that the value of the exponent $(\beta_1-\beta_2)$ in the equation (8) in case of the quantitative analysis of As is twice as large as that in case of the quantitative analysis of B.

According to the embodiment as mentioned above, by quantitatively correcting the actually measured secondary ion intensity with respect to the sample to be analyzed by using the correction function f(X), B in the surface layer of the Si substrate and As in the surface layer of the Si substrate can be quantitatively analyzed at an ultrahigh sensitivity without executing a pre-treatment of the sample, an improvement of the apparatus, or the like. The method according to the embodiment is extremely suitable as an evaluation method of a concentration distribution of impurities which were introduced in an ultrashallow region by various shallow doping techniques, a contamination state of the uppermost surface of the substrate, or the like.

By previously providing the quantitative correcting function as mentioned above for the secondary ion mass spectrometer, the quantitatively corrected SIMS analysis data can be directly obtained from the secondary ion mass spectrometer. As for various kinds of combinations of the element species and the matrices, the correcting function is derived on the basis of the results of the SIMS analyses regarding the standard samples. The quantitative correcting function based on the correcting function is previously provided for the secondary ion mass spectrometer. Due to this, for the various combinations of the element species and the matrices, the quantitatively corrected SIMS analysis data can be directly obtained from the secondary ion mass spectrometer.

Having described a specific preferred embodiment of the present invention with reference to the accompanying drawings, it is to be understood that the invention is not limited to that precise embodiment, that various changes and modifications may be effected therein by one skilled in the art without departing from the scope or the spirit of the invention as defined in the appended claims.

For example, although the embodiment have been described with respect to the case of quantitatively analyzing B in the Si substrate and the case of quantitatively analyzing As in the Si substrate, by preparing ion implantation standard samples similar to those mentioned above, and by executing the SIMS analysis, and by obtaining the correcting function based on the results of the SIMS analyses, for a combination of every element species and the matrices, the secondary ion yield which was influenced by the primary ion implantation effect is corrected. The absolute concentration distribution can be quantitatively obtained. Examples of combinations of element species matrices other than B/Si and As/Si are shown in the following Table 9.

TABLE 9

| Examples of Combinations of Matrices/Element Species | |
|---|---|
| Element Species | Matrix |
| P | Si |
| Sb | Si |
| B | $SiO_2$ |
| P | $SiO_2$ |
| As | $SiO_2$ |
| Si | GaAs |
| Zn | GaAs |

In addition to the materials mentioned in Table 9, a metal such as Al or the like or compound semiconductors other than GaAs can be also used as a matrix.

Although the above embodiment has been described with respect to the case where $^{32}O_2{}^+$ was used as a primary ion species, an element other than $^{32}O_2{}^+$ can be also used as a primary ion species. Such examples are shown together with $D_x$ in Table 10.

TABLE 10

| Primary Ion Species and Critical Depth $D_x$ | | | | | |
|---|---|---|---|---|---|
| Primary Ion Species | Effective Accelerating Energy (keV) | Primary Ion Irradiation Angle (°) | $R_P$ (nm) | $\Delta R_P$ (nm) | $D_x$ (nm) |
| $N^+$ | 5.3 | 30 | 11.7 | 6.5 | 23.4 |
| $N^-$ | 10.5 | 30 | 23.0 | 11.0 | 42.2 |
| $O^+$ | 5.3 | 30 | 11.3 | 7.0 | 24.1 |
| $O^-$ | 17.5 | 30 | 37.6 | 17.8 | 68.6 |
| $Ar^+$ | 10.5 | 30 | 12.9 | 5.9 | 23.1 |
| $Ga^+$ | 25.0 | 30 | 19.0 | 8.5 | 33.7 |
| $Xe^+$ | 10.5 | 30 | 9.3 | 3.1 | 14.4 |
| $Cs^+$ | 14.5 | 30 | 11.0 | 3.3 | 16.2 |

($N^+$ and $O^+$ are actually used as molecule-like ions)

As described above, according to the quantitative analyzing method by the secondary ion mass spectrometric method of the invention, a target element in the surface layer of a sample can be quantitatively analyzed without executing a pre-treatment of a sample such as a film formation or the like, an improvement of the apparatus, or the like.

According to the secondary ion mass spectrometer, a target element in the surface layer of the sample can be quantitatively analyzed.

What is claimed is:

1. A quantitative analyzing method by a secondary ion mass spectrometric method whereby a target element in a sample to be analyzed is quantitatively analyzed by the secondary ion mass spectrometric method, comprising the steps of:
   quantitatively analyzing said target element by the secondary ion mass spectrometric method with respect to a plurality of ion-implanted standard samples, while changing an implantation energy; and
   correcting a secondary ion intensity which is obtained with respect to said target element in the surface layer of said sample to be analyzed by the secondary ion mass spectrometric method on the basis of the results of the quantitative analyses with respect to said plurality of standard samples.

2. The quantitative analyzing method according to claim 1,
   wherein said sample to be analyzed is a silicon substrate containing in its surface layer at least one element selected from a group of B, As, P and Sb and
   wherein $^{32}O_2{}^+$ is used as a primary ion species.

3. A secondary ion mass spectrometer having a function such that a secondary ion intensity which is obtained with respect to a target element in the surface layer of a sample to be analyzed by a secondary ion mass spectrometric method is corrected on the basis of results such that said target element was quantitatively analyzed by the secondary ion mass spectrometric method with respect to a plurality of ion-implanted standard samples, while changing an implantation energy.

* * * * *